US008611986B2

(12) United States Patent
Wu

(10) Patent No.: US 8,611,986 B2
(45) Date of Patent: Dec. 17, 2013

(54) SYSTEM AND METHOD FOR ELECTROMAGNETIC NAVIGATION IN THE VICINITY OF A METAL OBJECT

(75) Inventor: Chunwu Wu, Texas Township, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/411,109

(22) Filed: Mar. 2, 2012

(65) Prior Publication Data

US 2012/0165660 A1    Jun. 28, 2012

Related U.S. Application Data

(63) Continuation of application No. 11/123,985, filed on May 5, 2005, now abandoned.

(51) Int. Cl.
*A61B 5/05* (2006.01)

(52) U.S. Cl.
USPC .. 600/424; 600/407; 324/207.11; 324/207.12; 324/207.13; 324/207.14; 324/232; 324/247; 324/262; 702/94.95

(58) Field of Classification Search
None
See application file for complete search history.

(56) References Cited

U.S. PATENT DOCUMENTS

| | | | |
|---|---|---|---|
| 3,983,474 A | 9/1976 | Kuipers |
| 4,054,881 A | 10/1977 | Raab |
| 4,287,809 A | 9/1981 | Egli et al. |
| 4,314,251 A | 2/1982 | Raab |
| 4,829,250 A | 5/1989 | Rotier |
| 4,945,305 A | 7/1990 | Blood |
| 5,347,289 A | 9/1994 | Elhardt |
| 5,453,686 A | 9/1995 | Anderson |
| 5,752,513 A | 5/1998 | Acker et al. |
| 5,879,297 A | 3/1999 | Haynor et al. |
| 6,073,043 A | 6/2000 | Schneider |
| 6,172,499 B1 * | 1/2001 | Ashe ........................ 324/207.12 |
| 6,427,079 B1 | 7/2002 | Schneider et al. |
| 6,528,989 B1 | 3/2003 | Hansen |
| 6,636,757 B1 | 10/2003 | Jascob et al. |
| 6,774,624 B2 | 8/2004 | Anderson et al. |
| 7,433,728 B2 | 10/2008 | Govari |
| 2003/0117135 A1 | 6/2003 | Martinelli et al. |
| 2003/0216639 A1 | 11/2003 | Gilboa et al. |
| 2004/0188616 A1 | 9/2004 | Wu et al. |
| 2004/0207389 A1 | 10/2004 | Nieminen et al. |
| 2005/0012597 A1 | 1/2005 | Anderson |
| 2006/0252987 A1 | 11/2006 | Hasegawa et al. |

FOREIGN PATENT DOCUMENTS

WO    03075749 A2    9/2003

OTHER PUBLICATIONS

PCT App. No. PCT/US2006/017053, International Search Report and Written Opinion of the ISA, Jan. 2007.

* cited by examiner

*Primary Examiner* — Unsu Jung
*Assistant Examiner* — Joseph M Santos Rodriguez

(57) ABSTRACT

A system and method for performing object localization based on the emission of electromagnetic fields. The electromagnetic fields are simultaneously emitted from different transmitters. One electromagnetic field is emitted at a base frequency; the remaining waves are emitted at frequencies that are harmonics of the base frequency. The composite magnetic fields are measured by sensors. The signal generated by each sensor is subject to a Fourier analysis to determine the strengths of the individual electromagnetic fields forming the composite electromagnetic field. These individual measure field strength data are then used to determine the position and orientation of the sensors relative to the transmitters.

20 Claims, 28 Drawing Sheets

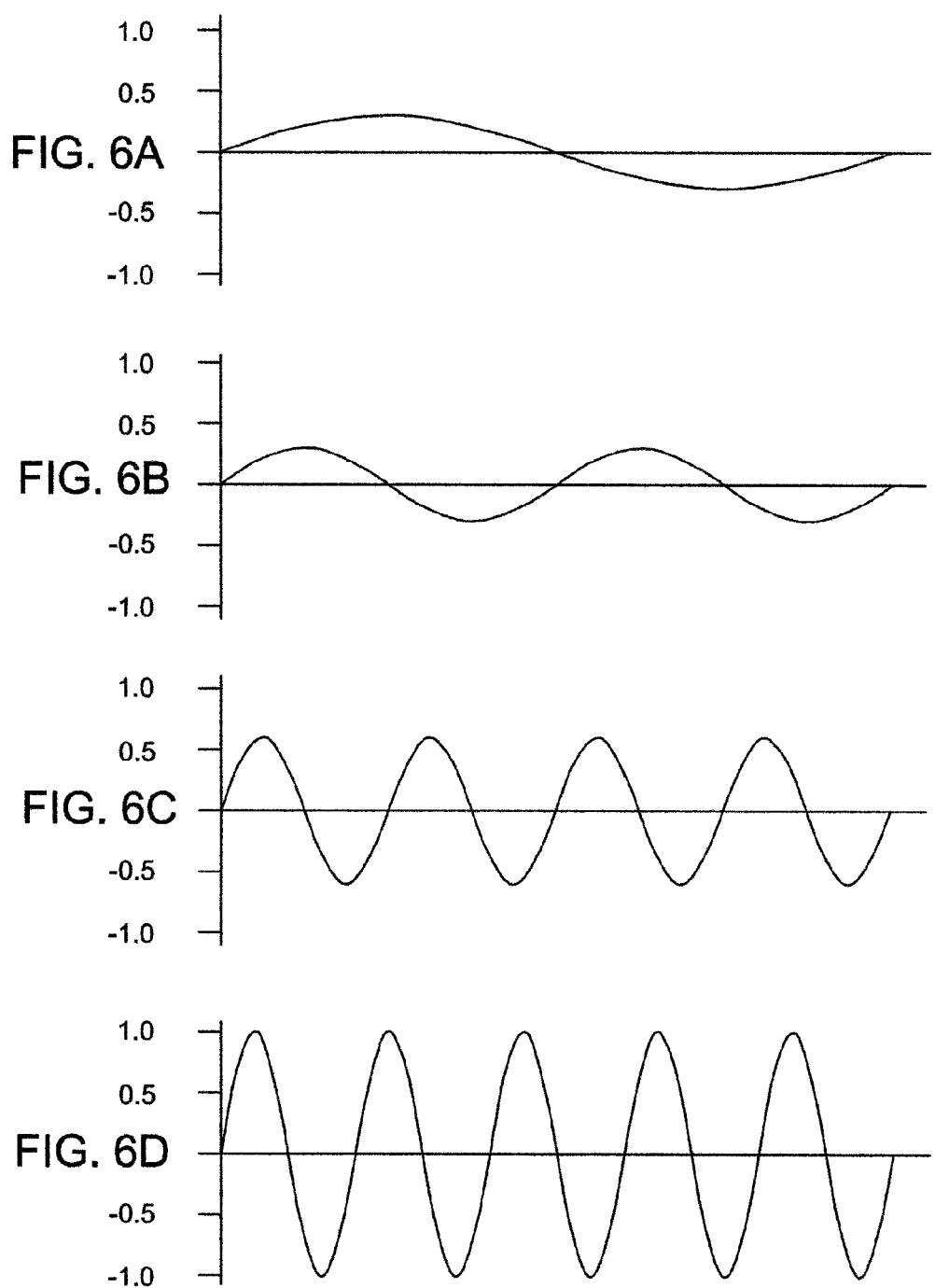

| TRNSMTR 26 | 20 Hz | 80 Hz | 40 Hz | 20 Hz | 80 Hz | 40 Hz |
|---|---|---|---|---|---|---|
| TRNSMTR 28 | 40 Hz | 20 Hz | 80 Hz | 40 Hz | 20 Hz | 80 Hz |
| TRNSMTR 30 | 80 Hz | 40 Hz | 20 Hz | 80 Hz | 40 Hz | 20 Hz |
| TIME | N | N+1 | N+2 | N+3 | N+4 | N+5 |

FIG. 10

| XMTR 26 | 80Hz | 20Hz | 80Hz | | | | |
|---|---|---|---|---|---|---|---|
| XMTR 28 | 100Hz | | | 20Hz | 100Hz | | |
| XMTR 30 | 140Hz | | | | | 20Hz | 140Hz |
| TIME | N | N+1 | N+2 | N+3 | N+4 | N+5 | N+6 |

FIG. 25

SYSTEM AND METHOD FOR ELECTROMAGNETIC NAVIGATION IN THE VICINITY OF A METAL OBJECT

RELATIONSHIP TO EARLIER FILED APPLICATION

This application is a continuation of application Ser. No. 11/123,985, now abandoned, the content of which, in its entirety, is incorporated herein by reference.

FIELD OF THE INVENTION

This invention is generally related to a system and method for determining the location of an object, such as the location of an object in a surgical field. More specifically, this invention is related to a system and method for determining the location of an object using electromagnetic radiation and in an environment where a metal object may be present.

BACKGROUND OF THE INVENTION

There are number of fields of human endeavor wherein it is useful, if not necessary, to know precisely the location and orientation of an object within a space. Surgery is one such field in which this information is desirable. Surgical navigation systems are available that enable medical personnel to know, with a high degree of precession, the location and orientation of surgical instrument or implant relative to a surgical site on the patient. Often this information is used in surgical procedures to facilitate the accurate removal and shaping of tissue. In an orthopedic surgical procedure, the information provided by the surgical navigation system ensures that an implant is precisely positioned.

Surgical navigation systems and other position-locating systems use different means to identify the locations and orientations of the objects they track. A number of commercially available surgical navigation systems rely on light tracking to determine the position of the tracked object. Some systems for include trackers that are attached to the objects being tracked. Each tracker emits a number of light beams. Often light is emitted in the infrared wavelengths. A static device, referred to as a localizer, has light sensitive-receivers. Based on the locations from which the individual light beams are received at a localizer, a processor, also part of the system, determines both the position and orientation of the tracker. Based on this information, the position and orientation of the device attached to the tracker is inferentially determined.

Often, at the start of a medical procedure, the position of the patient's body tissue is mapped into a memory integral with the processor. Based on these data and the inferential determination of the tracked object, the surgical navigation system presents an image on a display that indicates the position of the tracked object relative to the body tissue. This allows a surgeon to virtually "view" the position of the object that is otherwise be concealed by overlying tissue.

In an orthopedic surgical procedure, a surgical navigation system is also used to measure the range of motion of the body limb(s) subject to the procedure. These measurement data facilitate the fitting of the implant to the patient to increase the likelihood of successful outcome of the procedure.

Light-based surgical navigation systems work reasonably well for providing object location and orientation data in a surgical setting. Nevertheless, there is a drawback associated with these systems. A light-based navigation system requires a line-of-sight between the light emitting components and the light-sensitive localizer. If the line is broken, the ability of the system to provide object position and location data may be interrupted. Thus, medical personnel using such system must make a concerted effort to keep their own body parts as well as other surgical devices from entering into the space wherein such lines-of-sight may be present.

If the breaking of a line-of-sight results in the interruption of the generation of the object position and location data, it may be necessary stop the procedure until the system can again provide the data. Such delays reduce the overall efficiency of the surgeon performing the procedure. Moreover, such delays can increase the overall length of time it takes to perform the procedure. This is counter to an objective of modern surgical practice, to perform the procedure as quickly as possible. Surgeons work to this goal to reduce the amount of time the patient is held under anesthesia and his/her body is exposed and open to infection.

Recently, there have been efforts to employ electromagnetic field-sensing systems as surgical navigation systems. Generally, this type of navigation system includes one or more transmitters that emit electromagnetic fields. There is a sensor with one or more antenna sensitive to the electromagnetic fields. To provide both position and location information about an object, it is typically necessary to transmit plural fields and monitor the strength of each signal at plural antennae. Some of these transmitters emit electromagnetic fields upon being energized by AC drive signals. Others of these transmitters emit electromagnetic fields upon being energized by DC pulse signals. Based on the strength of the electromagnetic fields measured by the sensor, a processor determines the position and orientation of the sensor relative to the transmitter.

An electromagnetic navigation system does not require a line-of-sight path between the transmitter and sensor. Thus a surgeon could allow his/her arm to enter the space between the system's transmitter and sensor without being concern that such action will result in the interruption of the generation of the object position and orientation-defining data.

Nevertheless, care must be taken when using an electromagnetic navigation system, especially in a surgical setting. This is because metal objects exposed to electromagnetic waves from a first source, in turn, generate their own electromagnetic waves. When ferrous metals, such cold rolled steel, are exposed to magnetic waves, the metal itself becomes magnetized. The metal, in turn, generates its own magnetic fields. This added magnetic field is sensed by the sensor. This added magnetic field thus introduces an error into the magnetic field measurements made by the sensor.

Some metal, such as aluminum, copper, brass and 300 Series stainless steel are non-ferrous. When this type of metal is exposed to a changing magnetic field, a loop current, called an eddy current, develops around the metal. The eddy current, which is changes over time, generates its own magnetic field. This magnetic field, like the magnetic field generated by a ferrous metal object, can introduce an error into the magnetic field measurements made by the sensor.

In surgery, it is often necessary to introduce one or more metal instruments into the surgical in order to accomplish the desired procedure. Many of these instruments have metal parts. For the reasons discussed above, these instruments serve as sources of supplemental magnetic fields that introduce errors into the measurements made by the system sensor. These errors, in turn, can result in the system generating position and orientation information about the tracked object that may not be accurate. In a surgical procedure, and most other procedures in which such navigation is employed, such inaccuracies are wholly unacceptable.

A number of proposed systems sense and/or correct for the errors induced by the extraneous magnetic fields generated in the environment wherein the tracking is performed by electromagnetic field sensing. Some of these systems have transmitters that output AC signals. Some of these systems have transmitters that generate plural magnetic fields to each antenna. Systems wherein the transmitter includes plural parallel-aligned antenna have also been proposed. A disadvantage of many of these systems is that they require their complementary processors to perform numerous calculations in order to generate data representative of the "adjusted", eddy current-effect free, strength of the sensed magnetic fields.

Other proposed systems include providing the sensor unit with a calibration sensor. These systems thus require the addition of added component to device that it is desirable to keep as compact as possible. Moreover, these systems similarly require their processors to engage in numerous processing steps in order to produce output data representative of adjusted strength of the magnetic field.

Some of the proposed systems monitor the strength of the magnetic fields generated due to the generation of DC pulse currents. Some of these systems measure the magnetic field or the integral of the change in the magnetic field, $\int \partial B / \partial t$, at a time after the magnetic pulse is initially generated. The logic behind waiting this time period to make the measurement is that effects of the eddy currents will have attenuated to a nil level. One disadvantage of these systems is that it delays when, during the signal processing cycle, the magnetic field is measured. This delays when the processor is able to determine object position and orientation. Also, given the relatively long period in which the signal is emitted, these systems can only provide updated sensor position and orientation data at relatively slow frequencies.

Still others of these systems do not actually measure the actual magnetic field, its rate of change or any related integrals. These systems, instead, monitor the profile, the strength, of the magnetic field generated as a consequence of the initial emission of the DC pulse. Based on these measurements, a value representative of the eddy current-free magnetic field is calculated. The logic behind this process is that, since the effect of the eddy current diminishes over time, the initial plot of field strength should, in theory, serve as a basis for calculating the strength of the eddy current free magnetic field. In practice, it has been found that these calculations do not result in the determination of values that accurately represent eddy current-free magnetic field strength. Consequently, the accuracy of the object position and location data produced from these adjusted magnetic field strength data is open to question.

SUMMARY OF THE INVENTION

This invention is related to a new and useful system and method for determining the position and orientation of an object by using magnetic field sensing. The system and method of this invention relatively quickly generates object location and orientation data even in the presence of eddy current-induced magnetic fields. The invention also provides a means for determining whether or not extraneous magnetic fields, such as those generated by ferrous metal objects, are present in the space in which the object is being tracked. This notice makes it possible to take the steps necessary to eliminate the presence of these objects.

In one embodiment, the invention operates by simultaneously transmitting AC signal-induced magnetic fields. The signals applied to the transmitters that emit these fields are at a base frequency and at frequencies that are harmonics of the base frequency. In some versions of the invention, these signals are at low frequencies, below 1,000 Hz. This minimizes, if not eliminates, the effect of eddy current-induced magnetic fields.

In another version of the invention, the system simultaneously emits two sets of magnetic fields. One set of fields are emitted based on the application of relatively high frequency drive signals. These fields are the navigation magnetic fields. The second set of emitted fields is emitted based on lower frequency drive signals. These fields are the surveillance magnetic fields. In preferred versions of this embodiment of the invention, the lowest frequency AC surveillance drive signal is the base signal for both the surveillance and navigation drive signals. The remaining surveillance and navigation drive signals are harmonics of the base signal.

Based on the measured surveillance fields, the field strength of the measured navigation magnetic fields are corrected to compensate for the effects of the eddy current-induced fields. The measured surveillance fields are also used to determine whether or not the eddy-current induced magnetic fields are at an unacceptable high level.

In another version of the invention, the strengths of the navigation magnetic fields are, themselves, monitored to determine whether or not the eddy current-induced signals have reached an unacceptably high level.

Another embodiment of the system and method of this invention emits DC pulse-induced magnetic fields. A period of each magnetic field starting after the initial emission of the field is measured. Based on the strength of the field during the measured field, a value representative of the eddy current field-free measurement of magnetic field strength is calculated.

Another embodiment of the system of this invention is the invention has plural transmitters. The transmitters are in a fixed spatial relationship. The sensor unit receives the magnetic fields emitted by both transmitters. Based on the sensed magnetic fields, the system is able to determine whether or not ferrous metal object within space in which tracking is occurring affecting the ability of the system to track.

BRIEF DESCRIPTION OF THE DRAWINGS

The invention is pointed out with particularity in the claims. The above and further features and benefits of the invention are described in the following detailed description taken in conjunction with the accompanying drawings in which:

FIGS. 6A and 6B are plots of the surveillance drive signals that are simultaneously applied to each transmitter in order according the second AC embodiment of this invention;

FIGS. 6C, 6D and 6E are plots of the three navigation drive signals that are separately applied simultaneously to, respectively, the first, second and third transmitters as navigation drive signals;

FIG. 10 is a timing diagram illustrating the periods in which the different navigation drive signals are applied to the individual transmitters of the embodiment of the invention illustrated in FIG. 9;

FIG. 25 is a timing diagram illustrating a pattern for interleaving a surveillance signal with the navigation signals according to this invention.

DETAILED DESCRIPTION

I. Basics of Magnetic Field Sensing Navigation

Figure 1:
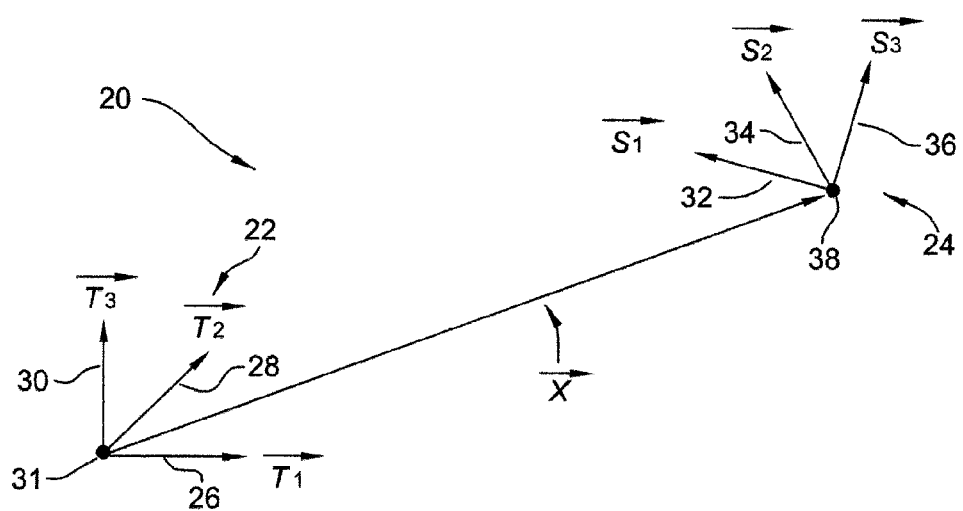
FIG. 1 is a diagrammatic illustration of the principles of tracking an object based on magnetic field strength.

FIG. 1 is a basic illustration of how a magnetic field sensing system is employed to determine the position and orientation of a tracked object. In the surgical field, such systems are called surgical navigation systems. In others fields of endeavor, these systems are referred to as object tracking systems, position measurement systems or object localization systems. Substantially all magnetic field sensing navigation systems, including system 20 of this invention, operate according to the basic principles now described.

Figure 1A:
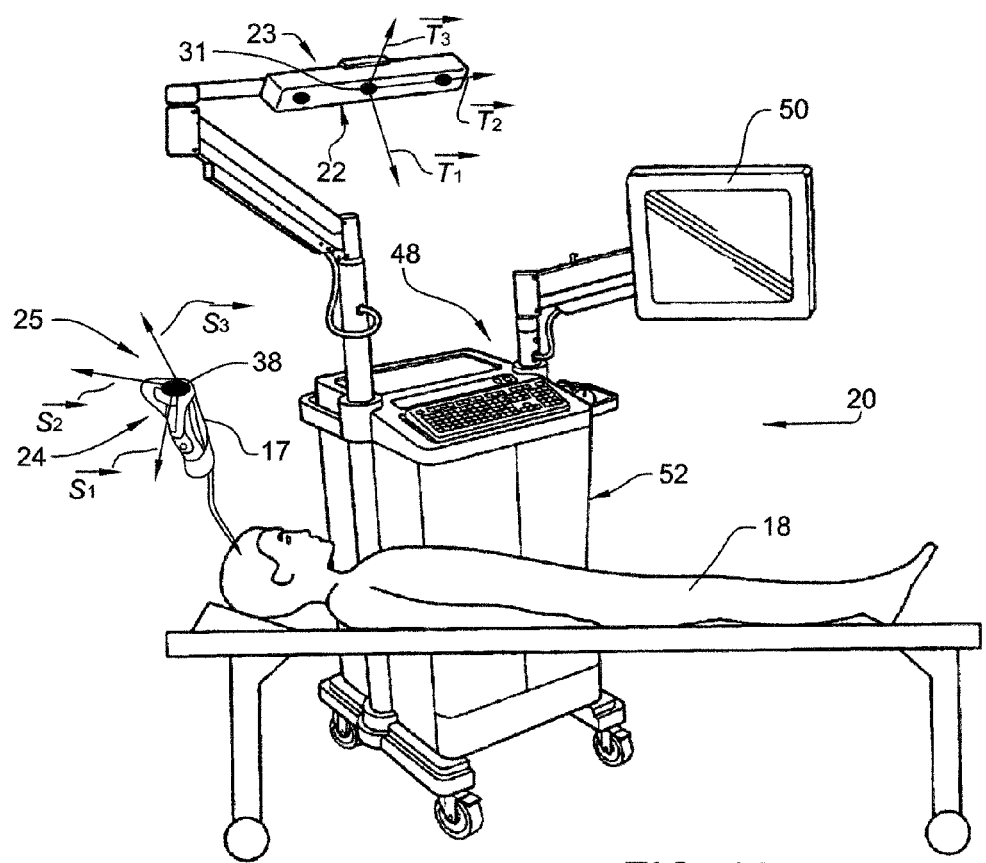
FIG. 1A is a perspective view of the components of a surgical navigation system constructed in accordance with this invention.

Generally, the system 20 includes a transmitter assembly 22 and a sensor assembly 24. Transmitter assembly 22 includes three transmitters, 26, 28 and 30 in the Figures. The transmitters 26, 28, and 30 are typically in the form of coils. The transmitters 26, 28, 30 are, ideally, mutually orthogonal relative to each other. In preferred systems, including systems of this invention, transmitters 26, 28 and 30 are centered on a common point, point 31 in the Figures. Mathematically, transmitters 26, 28 and 30 are represented by vectors $\vec{T}1$, $\vec{T}2$ and $\vec{T}3$, respectively. For mathematic derivation of this invention, we define a transmitter coordinate system 23 seen in FIG. 1A that has its origin at point 31 and its x-, y- and z-axis align along the vectors $\vec{T}1$, $\vec{T}2$ and $\vec{T}3$ of the transmitters 26, 28 and 30, respectively.

Sensor assembly 24 includes three sensors 32, 34, and 36 capable of monitoring the magnetic fields generated by the transmitter assembly 22. The individual sensors may be coils, flexgate transducers, magnetorsisitive sensors, Hall effect sensors or any other devices capable of providing precision measurements of magnetic fields. The individual sensors 32, 34 and 36 are, ideally, mutually orthogonal from each other. Ideally, especially in the system 20 of this invention, the sensors are also centered on a common point, point 38 in the drawings. Mathematically, sensors 32, 34 and 36 are represented by vectors $\vec{S}1$, $\vec{S}2$ and $\vec{S}3$, respectively. For mathematic derivation of this invention, we define a sensor coordinate system 25 (FIG. 1A) that has its origin at point 38 and its x'-, y'- and z'-axis align along the vectors $\vec{S}1$, $\vec{S}2$ and $\vec{S}3$ of the sensors 32, 34 and 36, respectively.

A typical navigation system 20 is constructed so that the transmitter assembly 22 is at a relatively fixed location. Thus, transmitters 26-30 are housed in a relatively static unit. Transmitter coordinate system 23, defined with position and orientations of transmitters 26-30, for reference purposes, is the system localizer. Sensor assembly 24 is attached to the object the position and orientation of which is to be tracked. In FIG.

1A, this object is a medical instrument 17. The unit containing sensors 32-36 is often referred to as the tracker. The sensor coordinate system 25, that define the position and orientations of sensors 32-36, for reference purposes, is the system tracker. For a typical navigation system, one uses one localizer 23. There are several trackers 25 (one shown). Each tracker 25 is used to track an individual object so that system tracks multiple objects. Thus, in the depicted system of FIG. 1A, the system is employed to determine the position of a surgical tool, instrument or implant relative to a surgical site on a patient 18.

Figure 3:
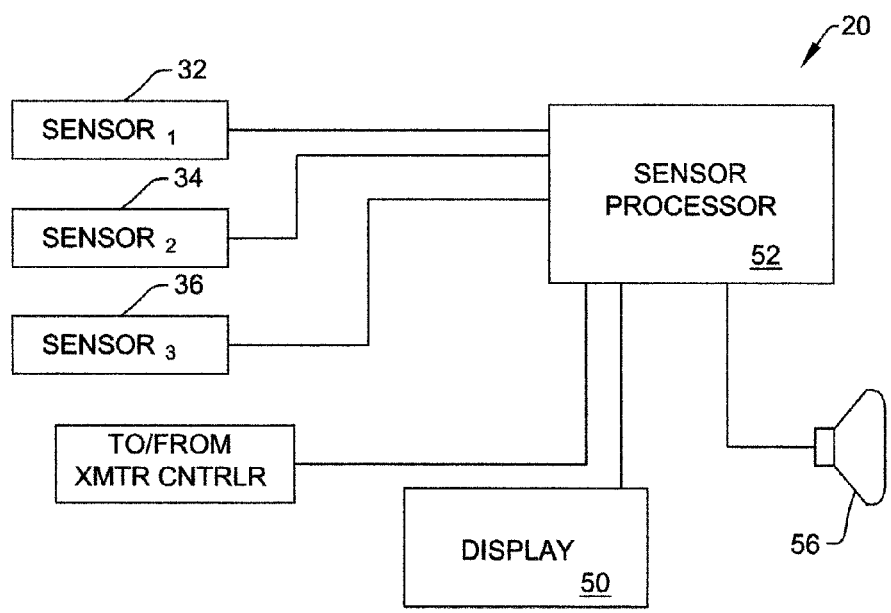
FIG. 3 is a block diagram of an idealized receiver assembly of the system of this invention.

Connectors, not shown, attach the transmitter assembly 22 to drive circuitry (not shown in FIG. 1). The measurements of magnetic field strength made by sensors 32-36 are applied to a sensor processor 52 (FIG. 3). Typically, this signal transfer is by a wireless RF connection. Other wireless signal transfer mechanisms such as infra-red connections may be used to establish some or all of these connections. Wired connections may also be employed.

In some alternative navigation systems, including systems of this invention, the transmitter assembly 22 is attached to the object to be tracked and the sensor assembly 24 is at a fixed location.

A primary goal of the navigation process is to determine the geometrical relationship between the transmitter coordinate system (localizer) 23 and the sensor coordinate system (tracker) 25. This makes it possible to transform position and orientation data in the sensor coordinate system (tracker) 25 to the transmitter coordinate system (localizer) 23, and vise verse. Using these transformations, all the objects tracked are placed in a common coordinate system even if the objects shift positions and orientations. The transformation that converts the coordinates in sensor coordinate system to that in transmitter coordinate system is represented by a translation vector $\vec{x}$ and a rotational matrix R. Here the vector $\vec{x}$ is the vector from point 31, the origin of transmitter coordinate system (localizer) 23 to point 38, the origin of sensor coordinate system (tracker) 25. This is also the coordinates of point 38 referred to transmitter coordinate system. The rotational matrix R represents the rotation that aligns the x-, y- and z-axes of transmitter coordinate system (localizer) 23 to the x'-, y'- and z'-axes of sensor coordinate system (tracker) 25. If we use $\hat{e}'_x$, $\hat{e}'_y$, $\hat{e}'_z$ to represent the unit vectors of, respectively, the x'-, y'- and z'-axes of the sensor coordinate system, referenced to transmitter coordinate system, rotational matrix R can be written as:

$$R = [\hat{e}'_x, \hat{e}'_y, \hat{e}'_z] = \begin{bmatrix} e'_{xx} & e'_{yx} & e'_{zx} \\ e'_{xy} & e'_{yy} & e'_{zy} \\ e'_{xz} & e'_{yz} & e'_{zz} \end{bmatrix} \quad (1)$$

Each matrix element $e'_{ij}$ is a component of the unit vector of sensor axis j projected to transmitter axis i.

Transmitters 26, 28 and 30 generate separate magnetic fields. The magnetic fields emitted by transmitters 26, 28 and 30 are represented as vectors $\vec{B}1$, $\vec{B}2$ and $\vec{B}3$, respectively. If each transmitter 26, 28 and 30 is considered to be a magnetic dipole, the particular magnetic field $\vec{B}i$ emitted by transmitter $\vec{T}i$ present at location $\vec{x}$ is defined by the equation:

$$\vec{B}i = \frac{3(\hat{x} \cdot \vec{T}i)\hat{x} - \vec{T}i}{|\vec{x}|^3} \quad (2)$$

Here, $\hat{x}$ is the unit vector along vector $\hat{x}$. The "●" operator is the vector dot product operator. The magnetic fields produced by transmitters 26, 28 and 30 are now referred to as navigation magnetic fields. Thus, the magnetic fields collectively present at point 38 are described by magnetic field matrix Bm, where:

$$B'm = [\vec{B}'1 \;\; \vec{B}'2 \;\; \vec{B}'3] = \begin{bmatrix} B'1_x & B'2_x & B'3_x \\ B'1_y & B'2_y & B'3_y \\ B'1_z & B'2_z & B'3_z \end{bmatrix} \quad (3)$$

The superscript apostrophe indicates that the magnetic fields are normalized to account for differences in magnetic strength of each transmitter.

Each sensor 32, 34 and 36, measures the strength of each of the three magnetic fields. Thus, at a given location and orientation, the following measurements are obtained:

$$\begin{bmatrix} m_{11} & m_{21} & m_{31} \\ m_{12} & m_{22} & m_{23} \\ m_{13} & m_{23} & m_{33} \end{bmatrix}$$

where $m_{ij}$ is the strength of the magnetic field based on the field emitted from transmitter i measured at sensor j. The above matrix is the measurement matrix M. Each measured value $m_{ij}$ of magnetic field strength is based on the magnetic field $\vec{B}i$ being measured by sensor $\vec{S}j$ according to the following formula:

$$m_{ij} = \vec{B}i \bullet \vec{S}j \quad (4)$$

Each sensor vector $\vec{S}j$ aligns with the associated axis j, unit vector $\hat{e}'_j$, in the sensor coordinate system.

Thus, the nine measured magnetic field values are used to solve for six unknowns, the three variables representative of position vector $\vec{x}$ and the three variables representative of the orientation of the sensor coordinate system (tracker) 25 and, therefore, the object to be tracked, relative to the transmitter coordinate system (localizer) 23.

Algorithms such as those provided in U.S. Pat. No. 4,287, 809, Helmut-Mounted Sighting System, issued 8 Sep. 1981, U.S. Pat. No. 4,314,251, Remote Object Position And Orientation Locator, issued 2 Feb. 1982 and U.S. Pat. No. 4,945, 305, Device For Quantitatively Measuring The Relative Position And Orientation Of Two Bodies In The Presence Of Metals Utilizing Direct Current Magnetic Fields, issued 31 Jul. 1990 are employed to, based on the magnetic field measurements, determine the position and orientation of the sensor assembly 24. Each of the above-cited documents is incorporated herein by reference. By induction, this leads to the knowledge of the position and orientation of the object attached to the sensor assembly. Often, especially with a surgical navigation system, this information is presented on a display 50 (FIG. 3).

In brief, though, it can be appreciated that, given Equation 4 above, the elements of the measurement matrix M' can be determined according to the relationship:

$$M' = \begin{bmatrix} m'_{11} & m'_{21} & m'_{31} \\ m'_{12} & m'_{22} & m'_{23} \\ m'_{13} & m'_{23} & m'_{33} \end{bmatrix} \quad (5)$$

$$= \begin{bmatrix} \vec{B}'1 & \vec{B}'2 & \vec{B}'3 \end{bmatrix}^T \cdot [\hat{e}'_x, \hat{e}'_y, \hat{e}'_z]$$

$$= B'm^T \cdot R$$

Here, the apostrophe of matrix M' indicates that the measurements of the matrix are normalized to account for differences in the efficiencies of the transmitters 26-30 and the differences in the sensitivities of the sensors 32-36. Superscript T denotes matrix transpose. The "·" operator indicates matrix multiplication. Thus, Equation 5 states that the measurements of the magnetic fields by all sensors 32-36 is related to the ideal dipole at the location of point 38, the origin of the sensor coordinate system (tracker) 38 by the rotational matrix R.

Moreover, Equation 5 also means that a common matrix A can be calculated from either the magnetic field measurements or the ideal dipole magnetic fields oriented at point 38. Matrix A is formed as:

$$A = M' \cdot M'^T = B'm^T \cdot R[B'm^T \cdot R]^T = B'm^T \cdot R \cdot R^T \cdot B'm = B'm^T \cdot B'm \quad (6)$$

Thus, matrix A is the product of the transpose of a 3×3 matrix and the matrix itself. Matrix A is therefore real and symmetric. Accordingly, matrix A can be diagonalized by calculating its eigenvalues and eigenvectors:

$$X^T \cdot A \cdot X = \lambda \quad (7)$$

Here, λ is a diagonal matrix with the eigenvalues as its diagonal terms. Matrix X is the orthogonal transformation matrix formed with all the orthornormal eigenvectors.

The eigenvector for the largest eigenvalue is the unit vector $\hat{x}$ in Equation 2 along vector $\vec{x}$ from point 31 (the original of the localizer) to point 38 (the origin of the tracker). The largest eigenvalue, $\lambda_{max}$, is related to vector $\vec{x}$ as:

$$|\vec{x}| = \sqrt[3]{\frac{2}{\sqrt{\lambda_{max}}}} \quad (8)$$

Thus, from the eigenvalues and associated eigenvectors of matrix A, unit vector $\hat{x}$ and $|\vec{x}|$, the length of vector $\vec{x}$ are known. This makes it possible to obtain vector $\vec{x}$ from:

$$\vec{x} = |\vec{x}| \hat{x} \quad (9)$$

From the determination of vector $\vec{x}$, the position of point 38 relative to point 31 is known. From knowledge of vector $\vec{x}$, Equations 2 and 3 are used to calculate matrix B'm. Equation 5 is then employed to calculate the rotational matrix R. This provides the orientation of the sensor coordinate system (tracker) 25 relative to the orientation of transmitter coordinate system (localizer) 23.

It should be further recognized that part of the signal processing includes normalizing the measurements of magnetic field strength. The magnetic field strength measurements are first normalized to account for differences in strength of the magnetic fields emitted by the individual transmitters 26, 28 and 30. The measured magnetic field strength signals are further normalized to account for variations in sensitivity of the individual sensors 32, 34 and 36. These normalized measurements of magnetic field strength are the measurements upon which the position vector $\vec{x}$ and rotational matrix R are calculated.

Figure 2:
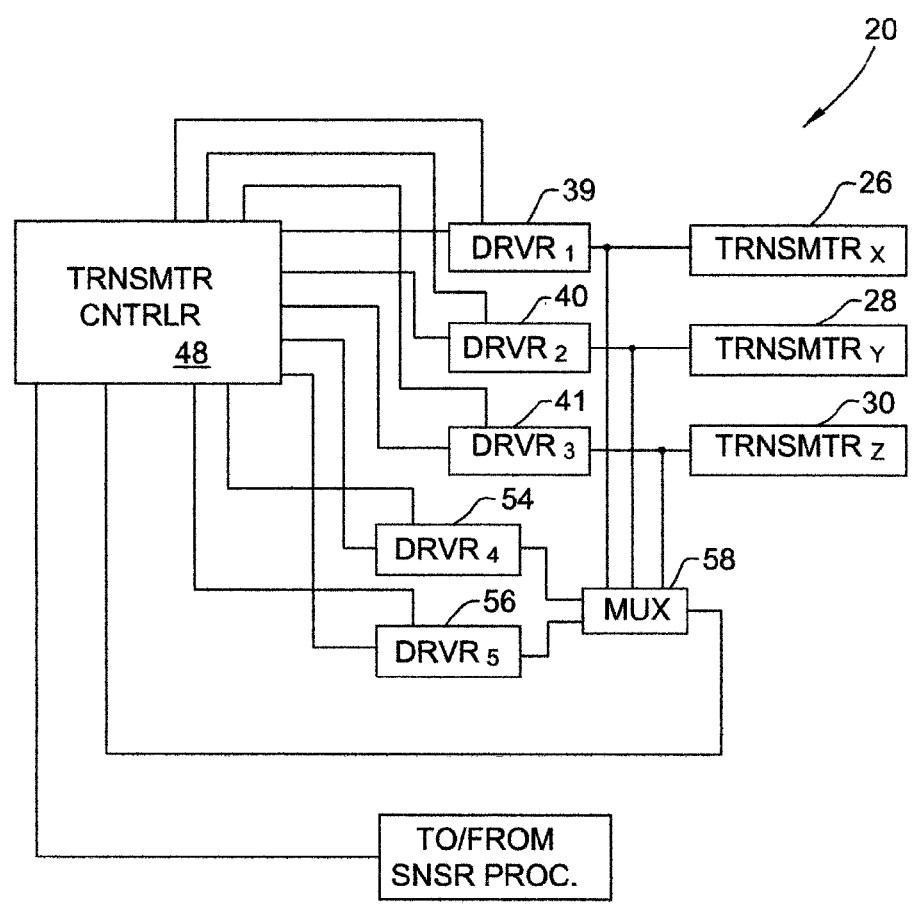
FIG. 2 is a block diagram of an transmitter assembly of the system of this invention.

II. Basic AC-Generated Magnetic Field Sensing System and Method of the Invention FIG. 2 illustrates the components of system 20 of this invention that cause transmitters 26, 28 and 30 to emit magnetic fields. Three drivers 39, 40, and 41 connected to the individual transmitters 26, 28, and 30, respectively. Each driver 39, 40 and 41 generates a specific frequency AC signal to the transmitter 26, 28 and 30, respectively, to which the driver is connected.

Figure 4A:
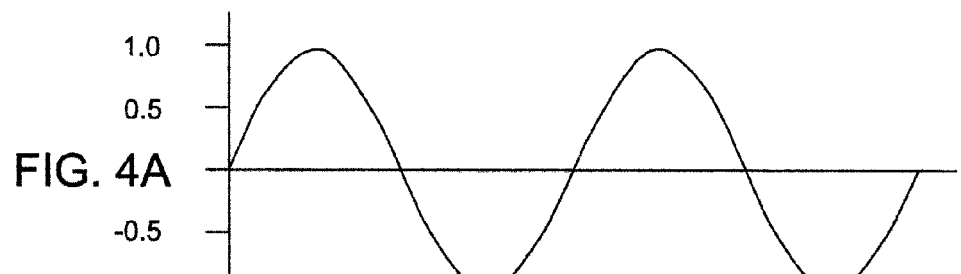
FIGS. 4A, 4B and 4C are plots of the base drive signals applied to a first transmitter and two of its harmonics which are applied as drive signals to, respectively, the second and third transmitters as drive signals.
Figure 4B:
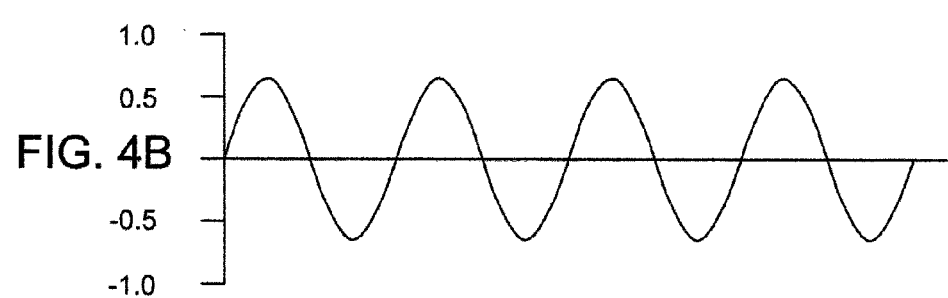
Figure 4C:
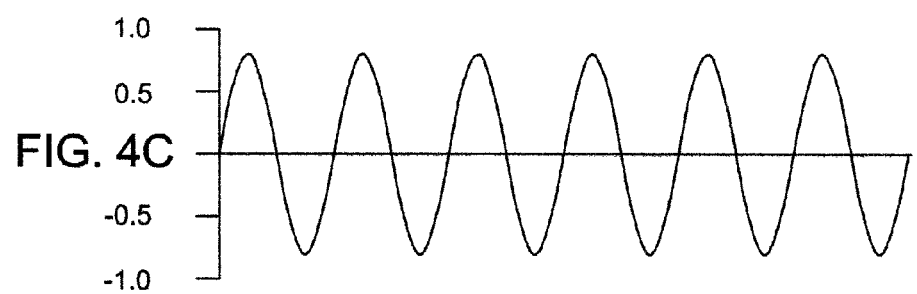

The frequencies of the AC signals generated by the drivers 39, 40 and 41 are different from each other and in a specific relationship. More particularly, one of the drivers 39, 40 or 41 generates a signal at the first harmonic of a base frequency. The remaining two drivers generate signals at frequencies that are second and higher harmonics of the base frequency. By way of example, driver 39 generates the signal at the base frequency, as represented by FIG. 4A, and the base frequency is 25 Hz. Driver 40 generates a signal at 50 Hz as represented by FIG. 4B. Driver 41 generates a signal at 75 Hz as represented by FIG. 4C. In the Figures, the signals emitted by drivers 39, 40 and 41 are shown as being in phase. This is for purposes of illustration. In practice, emitting the signals in phase simplifies some of the signal processing. However, there is no requirement that the signals or the navigation magnetic fields be emitted in phase.

To ensure that the signals generated by the drivers 39, 40 and 41 are in a harmonic relationship, a common frequency generator generates the base sine waves that are, in turn, amplified by the driver. In the illustrated version of the invention, this function is performed by a transmitter controller 48. This controller may, for example, be a DSP controller that generates three sine waves with defined frequencies. In FIG. 2, two conductors are shown as extending from the transmitter controller 48 to each driver 39-41. Two conductors are shown to illustrate that, in some versions of the invention, transmitter controller 48 in addition to supplying each driver 39-41 with a base signal at a select frequency also asserts control signals that regulate the actuation of the driver.

The output signals generated by sensors 32, 34, and 36 of sensor assembly 24 are applied to a common sensor processor 52, also part of system 20, seen in FIG. 3. While not shown, it should be appreciated that, prior to the application of each sensor signal to processor 52, the signal may be subjected to DC filtering to eliminate DC components, band pass filtering to eliminate noise and digitized. Each signal may, prior to or after digitization, may also be subjected to a variable gain amplification. This amplification may be performed to compensate for differences in sensitivities of the individual sensors 32, 34 and 36. Performing this individual amplification may eliminate the need to normalize the measurements of magnetic field strength otherwise performed to compensate for differences in sensor sensitivity.

Sensor processor 52 is also the component of the system 20 that, based on the measured signals representative of magnetic field strength, generates the position and orientation data for the tracked object. This is the data presented on display 50. In some versions of the invention, for example, the version depicted in FIG. 1A, a single hardware unit or sub-assembly collectively functions as transmitter controller 48 and sensor processor 52. In versions of the invention wherein the transmitter controller 48 and sensor processor 52 are separate components, these components are connected together. Generally, the transmitter controller 48 forwards data to the sensor processor 52 indicating the type of and when electromagnetic fields are emitted. Based on these data, the sensor processor 52 performs the processing steps discussed below.

Figure 4D:
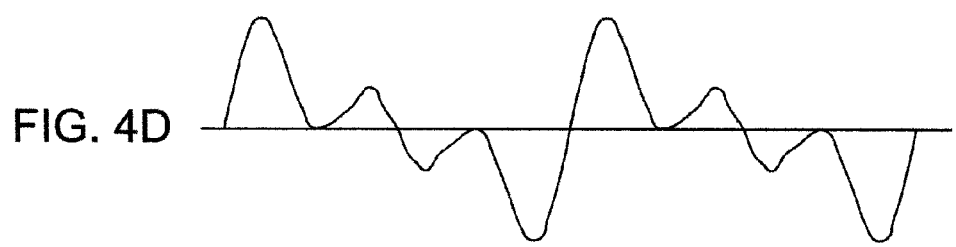
FIG. 4D is a plot of the composite magnetic field sensed at a single sensor of the sensor assembly.
Figure 5:
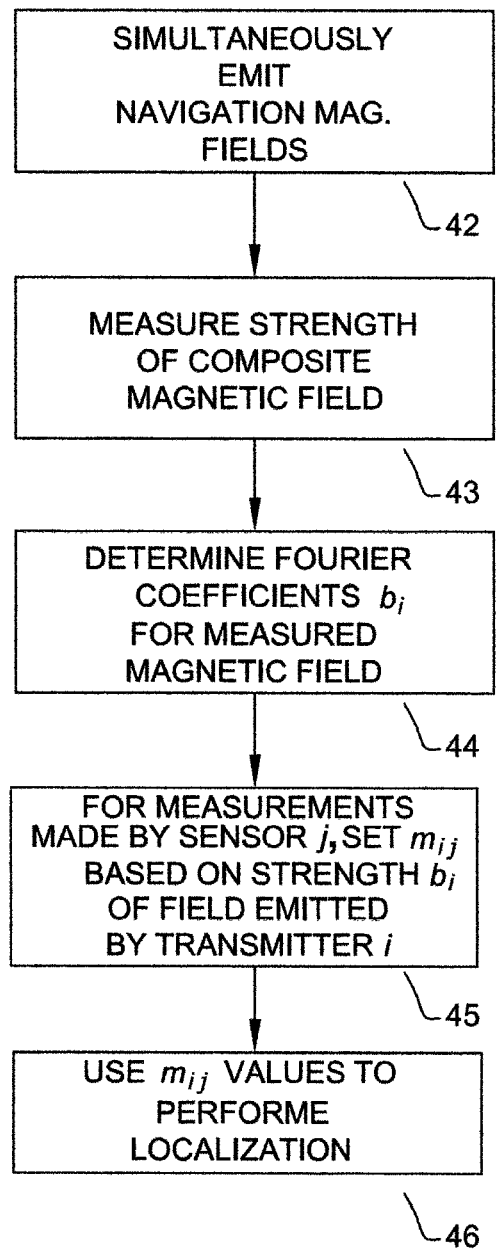
FIG. 5 is a flow chart of a basic method of object localization of this invention when AC signal-based magnetic fields are emitted.

In the basic system 20 and method of this invention, drivers 39, 40 and 41 simultaneously output the individual AC signals to their respective transmitters 26, 28, and 30. Transmitters 26, 28 and 30 therefore simultaneously emit navigation magnetic fields; each transmitter emits a navigation magnetic field at a distinct frequency, step 42 in FIG. 5. Each sensor 32, 34 and 36 simultaneously monitors the strength of a composite electromagnetic field that is the sum of the individual fields, step 43. FIG. 4D is representative of a sensor output signal representative of composite measured electromagnetic field strength made by one of the sensors 32, 34 or 36. FIG. 4D, it is noted shows the composite signal for two periods of the base frequency.

Figure 4E:
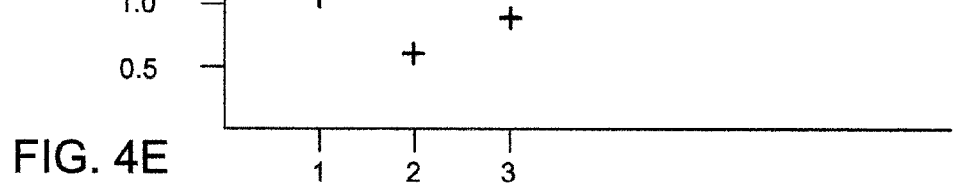
FIG. 4E is a plot of results of a Fourier transformation of the signal of FIG. 4E.

The signal representative of the strength of the composite measured magnetic field generated by each sensor 32, 34 and 36 is forwarded to the sensor processor 52. Sensor processor 52, in turn, performs a Fast Fourier Transformation (FFT) on each of composite signal, step 44. The coefficients $b_{ij}$ of the signal harmonics yielded in this transformation represent the strengths of the individual navigation magnetic fields that form the composite signal. FIG. 4E represents the coefficients generated as a result of the Fourier transformation of the signal of FIG. 4D that is, the signal over a period at least equal to one period of the base frequency. Thus, by way of example, the FFT of the signal produced by the sensor 34, the y-axis signal, yields three coefficients. The individual first, second and third component coefficients $b_{1y}$, $b_{2y}$, and $b_{3y}$, are representative of the measurements, $m_{1y}$, $m_{2y}$, and $m_{3y}$, of the strengths of $\vec{B1}$, $\vec{B2}$ and $\vec{B3}$, the three magnetic fields measured by sensor 34. Sensor processor 52 thus sets the measurements of magnetic field strength $m_{ij}$ based on the calculated $b_{ij}$ coefficients, step 45. Once these field strength determinations are made, sensor processor 52, in step 46, uses these data to execute the position and orientation-determining algorithms to determine the position and orientation of the sensor coordinate system (tracker) 25 relative to the transmitter coordinate system (localizer) 23.

When the system 20 and the method of this invention is employed, the FFT provides fast means for determining the strengths of the three magnetic fields sensed at each sensor 32, 34 and 36. Since the navigation magnetic fields are emitted at a base signal and its harmonics, the FFT quickly executes and the resultant coefficients are accurate representations of measured magnetic field strength. This makes it possible to, after the sensor measurements are made, to quickly and accurately determine the position and orientation of the sensor coordinate system (tracker) 25.

System 20 and the method of this invention is further arranged so that, in preferred versions of the highest frequency drive signal applied to any individual transmitter in 1,000 Hz or less. In more preferred versions of the invention, the highest frequency drive signal is at 300 Hz or less. In still more preferred versions, the highest frequency drive signal is 150 Hz or less. The application of these low frequency (100 Hz to 1 kHz) and/or very low frequency drive signals (100 Hz or less) to the transmitters 26-30 is that the transmitters, in turn, generate navigation magnetic fields at corresponding low or very low frequencies.

The reason it is desirable to emit the navigation magnetic fields at these frequencies is that the strength of the magnetic fields, $\vec{B}_e$, developed as a consequence of the generation of eddy currents is directly proportional to the frequency of the magnetic field(s) in the environment wherein the eddy-current producing object is located. It has been determined that, when the magnetic field is emitted at a frequency of 100 Hz or less, the effects of the eddy current-induced magnetic field is often negligible.

Thus, by operating system 20 so the magnetic fields are emitted at low or very low frequencies, most ideally at 100 Hz and below, the likelihood that the presence of any eddy current-induced magnetic field generating object in the space where the tracking is occurring, the "navigation" space, is often nil.

Another preferred method of operating system 20 is to operate the system so that none of the drivers generate signals at line voltage 60 Hz or at frequency of one of its harmonics. This avoids having to remove from the magnetic field measurements, magnetic field components emitted by electrical equipment into the navigation space space. Thus, if system 20 operates wherein the base frequency of drive signal generated by one of the drivers 39, 40 or 41 is 30 Hz, the remaining two drivers should output drive signals at 90 and 150 Hz, respectively. For international operation, i.e., operation outside of North America, signals should not be generated at 50 Hz or harmonics of this frequency.

III. AC-Generated Magnetic Field Sensing System and Method Capable of Eddy Current Monitoring and Correction In one alternative embodiment of this invention, system 20 both monitors and corrects for magnetic fields that develop as a consequence of the generation of eddy currents.

This version of the invention employs the two additional drivers 54 and 56 illustrated in FIG. 2. Drivers 54 and 56 generate AC surveillance drive signals. Drivers 39, 40 and 41 thus output the AC navigation drive signals. One of the drivers 54 or 56 generates a constant frequency signal referred to as the base signal. The remaining drivers, the drivers the generate the navigation drive signals, drivers 39-41, and the remaining surveillance signal driver 56 or 54, output signals at harmonics of the base drive signal. The signal output by the second surveillance signal driver is at a frequency lower than the frequencies of the signals output by the navigation signal drivers 39-41.

The signals output by surveillance signal drivers 54 and 56, are at power levels lower than those at which navigation signal drivers 39-41 output the navigation signals. Typically, the power level of the signals produced by the surveillance signal drivers 54 and 56 is between ⅓ to ½ of the power levels of the signals output by the navigation signal drivers 39-41.

By way of example, in one version of the invention, surveillance driver 56 outputs a 20 Hz signal, the first harmonic of a base signal of 20 Hz. The second surveillance driver, driver 54 outputs a second surveillance signal at 40 Hz. The three navigation signal drivers, drivers 39, 40 and 41, output signals at, 80, 100 and 140 Hz, respectively, higher order harmonics of the base signal. Per the above discussion, drivers 39-41 do not output signals at 60 Hz, or its first harmonic, 120 Hz.

The pair of surveillance drive signals is simultaneously applied in sequence to each of the transmitters 26, 28, and 30. In FIG. 2, the application of the surveillance signals to the drivers is shown through a multiplexer 58. Transmitter controller 48 generates control signals to the multiplexer 58 to establish to which transmitter 26, 28 or 30 the surveillance drive signals are sent simultaneously.

Figure 6E:
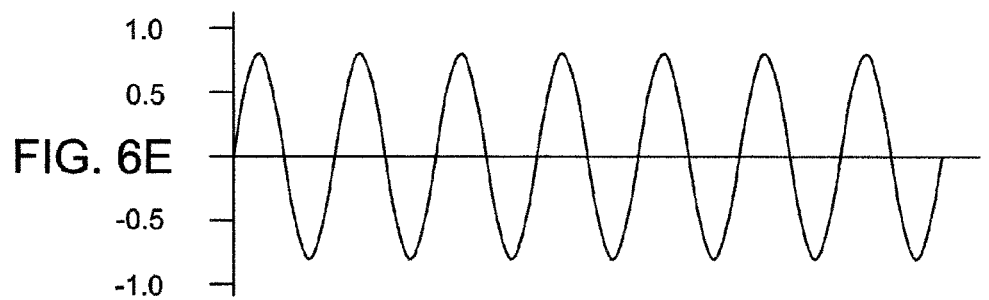
Figure 6F:
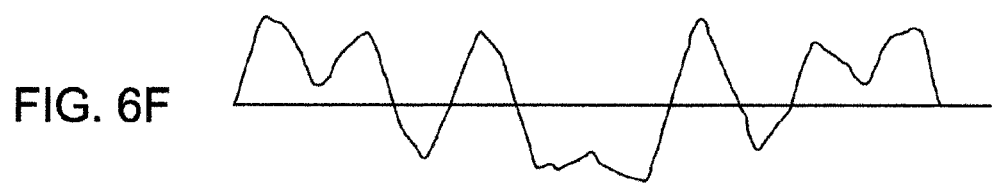
FIG. 6F is a plot of the composite magnetic field sensed by a single sensor of the second AC embodiment of this invention.
Figure 7:
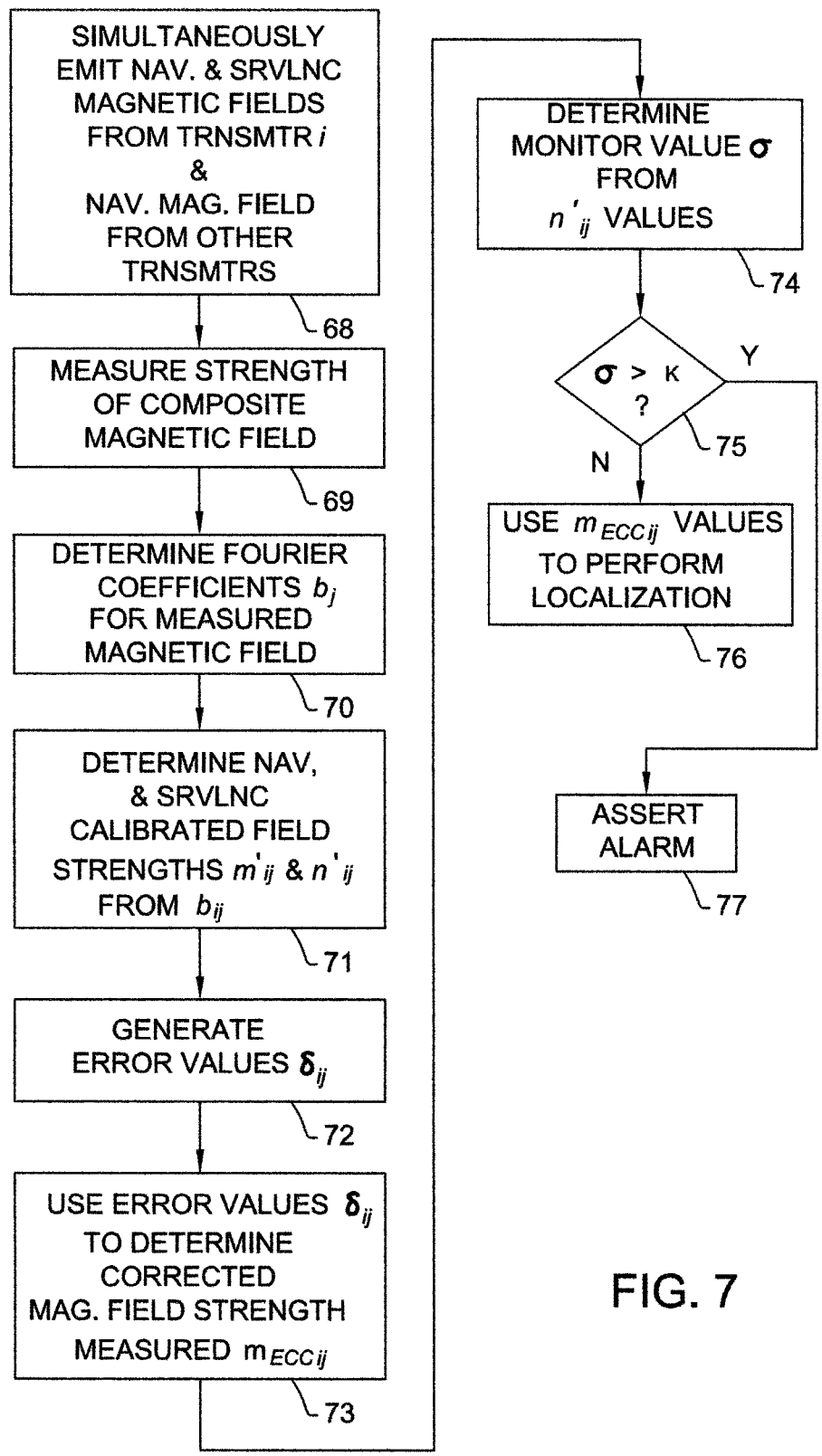
FIG. 7 is a flow chart of the process steps executed according to the second method of object localization of this invention when AC signal-based magnetic fields are emitted.

During the operation of this version of system 20, the pair of surveillance signals is simultaneously added to an individual one of the navigation drive signals for a select period of time, step 68 of FIG. 7. In some versions of the invention, this period may be between 5 and 500 ms. In more specific versions of the system 20, the surveillance signals are added for a period of 50 ms. The actual time period in which the surveillance drive signals are added varies inversely with the frequency of the navigation drive signals. After being added to a first one of the navigation drive signals, the surveillance drive signals are, in sequence, added to the second and third navigation drive signals before the cycle repeats. Thus for a set period of time, the magnetic field measured be each sensor 32, 34 and 36 is a composite of the three navigation magnetic fields and the two surveillance magnetic fields. This is seen by FIGS. 6A-6F. Here, FIG. 6A represents the base surveillance magnetic field emitted (the 20 Hz signal) by a particular transmitter 26, 28 or 30 when the lowest frequency surveillance drive signal is applied to the transmitter. FIG. 6B represents the second surveillance magnetic field emitted (the 40 Hz signal) by the same transmitter. FIGS. 6C, 6D and 6E, represent the three navigation magnetic fields emitted, respectively by the transmitters, 26, 28 and 30, at respectively, 80, 100 and 140 Hz.

Also in step 68, the remaining transmitters 26, 28 and 30 emit the navigation magnetic fields they normally emit.

Figure 6G:
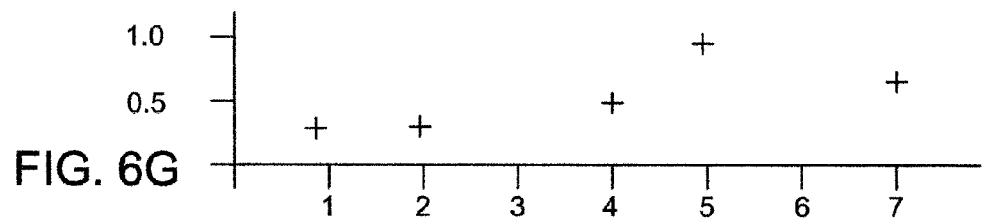
FIG. 6G is a plot of results of a Fourier transformation of the signal of FIG. 6F.

As with the basic version of the invention, each sensor 32, 34 and 36 generates an output signal that is the composite of the received emitted magnetic fields, step 69. The composite signal of FIG. 6F is a composite of the two surveillance magnetic fields and the three navigation magnetic fields. The FFT is used to decompose the output composite sensor signals, step 70. FIG. 6G represents the five coefficients produced by the FFT of the. Here, the coefficients of the first and second components of the composite signal represent, respectfully, the strengths of the surveillance magnetic fields. The coefficients of the third, fourth and fifth components represent the strengths of the three navigation magnetic fields.

In step 71, a two-step process is employed to calibrate the magnetic field measurements. This calibration, it is understood, is performed in addition to any normalization employed to compensate for differences in the strengths of the emitted navigation magnetic fields and the sensitivities of the sensors. In a first sub-step, both the navigation magnetic field strength signals, the $m_{kj}$ measurements, and the surveillance magnetic field strength measurements, $n_{kj}$ measurements, are adjusted to account for the fact that the sensor assembly 24 responds differently when exposed to fields with appreciably different frequencies. For the navigation magnetic field measurements, k=4, 5, or 7; this is representative of the fact that the navigation magnetic fields are emitted at frequencies that are, respectively at the fourth, fifth and seventh harmonics of the base frequency. For the surveillance magnetic fields, k=1 or 2; this is representative of the fact that the surveillance magnetic fields are emitted at the base frequency (unity) or its first harmonic.

Calibrated measurement signals, $m'_{kj}$ and $n'_{kj}$ are produced according to the following formulas:

$$m'_{kj} = m_{kj} c_{kj} \tag{10}$$

where $c_{kj}$ is the calibration factor for the field k=4, 5 or 7 (the navigation magnetic fields) at sensor j at which the measurement is made; j=1 2 or 3.

$$n'_{kj} = n_{kj} c_{kj} \tag{11}$$

where $c_{kj}$ is the calibration factor for field k; k=1 or 2, the surveillance magnetic fields at sensor j at which the measurement is made; j=1, 2 or 3.

The $c_{kj}$ values for both the navigation and surveillance magnetic fields are determined empirically prior to use of the system 20.

A second calibration is then performed on the initially calibrated surveillance magnetic field measurements. This calibration adjusts for the fact that the strengths of the surveillance magnetic fields are lower than that of the navigation magnetic fields. This calibration produces a finally adjusted surveillance magnetic field strength measurement $n''_{kj}$ according to the formula:

$$n''_{kj} = n'_{kj} d_k \tag{12}$$

where $d_k$ is the power adjust factor for the specific surveillance field and is the invert of the ratio in the difference between in power output from the surveillance signal driver and a "normalized" navigation signal driver, k=1 or 2.

These calibrated measurements are used to produce eddy-current corrected magnetic field strength measurements, step 72 of FIG. 7. These corrected measurements are produced by first generating error values for the measurements. These error values are generated for the navigation magnetic field emitted by each transmitter based on the surveillance magnetic fields simultaneously emitted from the transmitter. For example, the error factors for the measurements based on the navigation magnetic field emitted by transmitter 30 (here k=7) are generated according to the following formula:

$$\delta_{7j} = m'_{7j} - [(n''_{1j} + n''_{2j})/2] \tag{13}$$

where $\delta_{7j}$ is the error value for the magnetic field emitted by transmitter 30 at j=1, 2 or 3, j being the sensor at which the measurement of field strength is made.

The individual error values are based on the following relationship. As set forth above, at low frequencies the eddy current-induced magnetic field effect is proportional to frequency, $$\vec{B}_e \propto |\omega| \tag{14}$$

where ω is the frequency of the magnetic field to which the object that produces eddy current is exposed. At low frequencies, especially frequencies of 500 Hz and less, and more especially at frequencies of 300 Hz or less, there is a linear relationship between the strength of the measured eddy current magnetic field, and the frequency of the field to which the eddy current-producing object is stored.

Thus, when no eddy current-induced magnetic fields are present, the calibrated measured strengths of the magnetic fields remain constant with frequency. This is represented by line 80 of FIG. 8. On line 80, the strengths of the two surveillance magnetic fields and the navigation magnetic field (here the field emitted from transmitter 30) are represented by points 81, 82 and 83. Given the equal strengths of these magnetic fields at a given point, the error value, $\delta_{7j}$, is zero.

However, in a situation where an eddy current-producing object is in or near the navigation space, the added eddy current-induced magnetic field is present. The strength of the eddy current-induced magnetic field, in the above-discussed frequency range, linearly increases with frequency as represented by line 84 of FIG. 8. Line 84, it should be understood, represents the composite strength of the emitted surveillance or navigation magnetic field and the eddy current-induced magnetic field. The strengths of the calibrated measured surveillance fields, represented by points 85 and 86 on line 84, are less than strength of the calibrated measured navigation field, represented by point 87.

However, the corrected measurements of strength of the surveillance magnetic fields when the system is in this condition, are very close to the field strength measurements when there is no eddy current-induced magnetic field. (In FIG. 8, the differences are exaggerated for purposes of illustration.)

Figure 8:
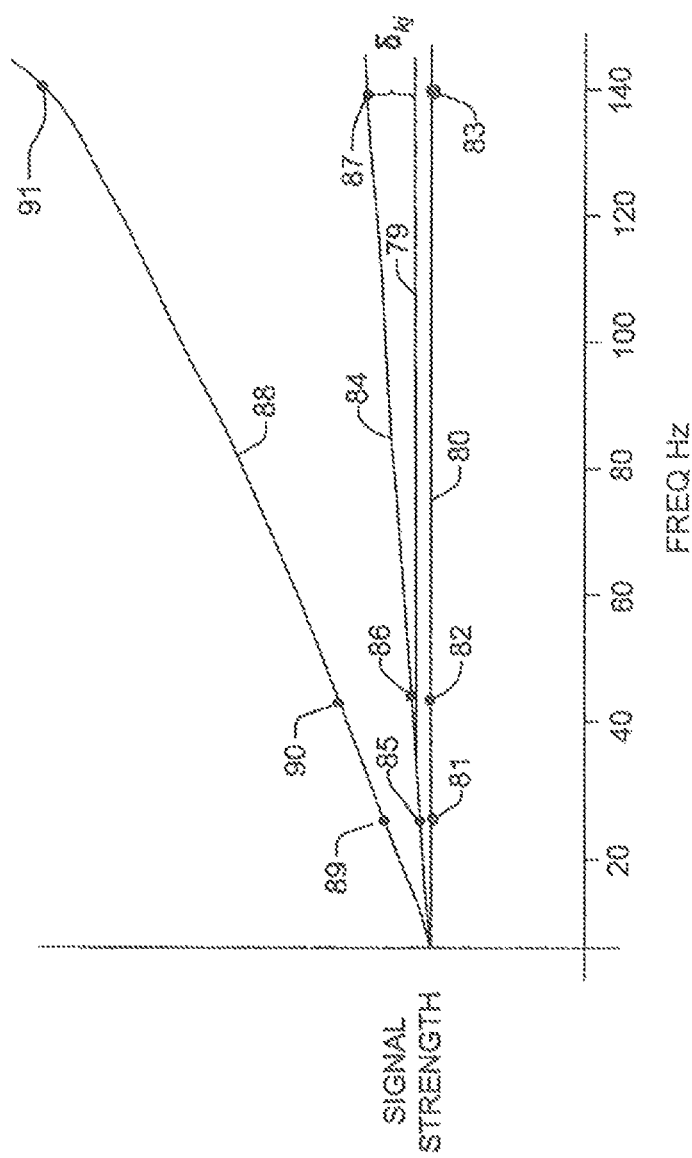
FIG. 8 is a graphical representation of the strength of eddy current-induced magnetic fields as function of frequency of the transmitter inducing the generation of the eddy current.

Therefore, for the purposes of generating error values, the $(n''_{kj}+n''_{kj})/2$ component of the error value generation equation represents the strength of the magnetic field that would be measured if the eddy current-induced magnetic field is not present. This value is an average of strengths of the two surveillance magnetic fields. This value is represented in FIG. 8 by line segment 79.

The error value $\delta_{kj}$ thus represents the difference between the measured strength of the navigation magnetic field and a value representative of the field strength in an eddy current-free environment.

Consequently, nine error values $\delta_{ij}$ are obtained. In step 73, these values are subtracted from the normalized measurements of magnetic field strength:

$$\begin{bmatrix} m'_{11} & m'_{21} & m'_{31} \\ m'_{12} & m'_{22} & m'_{32} \\ m'_{13} & m'_{23} & m'_{33} \end{bmatrix} - \begin{bmatrix} \delta_{11} & \delta_{21} & \delta_{31} \\ \delta_{12} & \delta_{22} & \delta_{32} \\ \delta_{13} & \delta_{23} & \delta_{33} \end{bmatrix} = \begin{bmatrix} m_{ECC_{11}} & m_{ECC_{21}} & m_{ECC_{31}} \\ m_{ECC_{12}} & m_{ECC_{22}} & m_{ECC_{32}} \\ m_{ECC_{13}} & m_{ECC_{23}} & m_{ECC_{33}} \end{bmatrix} \quad (15)$$

Here, a matrix element $m'_{ij}$ is a calibrated measurement of magnetic field strength. A matrix element $m_{ECCij}$ is an eddy current-corrected measurement of navigation signal magnetic field strength of the field generated by transmitter i as measured by sensor j. The matrix containing the $\delta_{ij}$ values is referred to as the error matrix, $\Delta$. The calibrated and eddy current corrected measurements of navigation signal magnetic field strength, the $m_{ECCij}$ measurements, are then used in step 76 to determine position and orientation of the sensor coordinate system (tracker) 25. In FIG. 7, this process is represented by step 76. Steps 74 and 75 that occur between steps 73 and 76 are discussed below.

In executing the above process, it is not recommended the $n''_{1j}$ and $n''_{2j}$ calibrated measurements of surveillance magnetic field strength be extrapolated to a 0 Hz a theoretical zero eddy current-induced magnetic field measurement. This is because the system error is assumed to be $\pm\delta$ at the surveillance frequencies. If the surveillance magnetic field strength is extrapolated to 0 Hz, the error value becomes $\pm3\delta$. Thus, the noise is amplified three times before there is error correction.

This version of the system and method of this invention is further configured to detect when, the strength of the eddy current-induced magnetic field is so strong that the error correction process cannot be employed to attenuate its effect. Specifically, as seen by plot 88 of FIG. 8, there may be situations when the strength of the eddy current-induced magnetic field is so great at frequencies of interest, field strength increases very rapidly with frequency. As seen by the right end of plot 88, at the higher range of the frequencies-of-interest, the increase in field strength with frequency may even shift from linear to exponential. When this occurs, as represented by points 89 and 90 on curve 88, the difference measured strength of the two surveillance magnetic fields is significant. Also, given the non-linear change in eddy current strength with frequency, represented by point 91 on plot 88, the error correction values are not able to accurately produce eddy-current-corrected measures of navigation magnetic field strength.

Therefore, in this version of system 20 of this invention, sensor processor 52 generates a monitor value $\sigma$, step 74 of FIG. 7. Monitor value $\sigma$ is representative of strength of the eddy current-induced magnetic field measured by the sensor 32, 34 or 36. The monitor value is calculated according to the formula:

$$\sigma = 1/3 \sum_{j=1}^{3} |(n'_{1j} - n'_{2j})| \quad (16)$$

Monitor value $\sigma$ is thus the average difference in surveillance field strength over the three sensors 32, 34 and 36. In preferred versions of this embodiment of the invention, the monitor value $\sigma$ is calculated each time error matrix $\Delta$ is calculated. The monitor value $\sigma$ is compared to a predetermined threshold value $\kappa$, step 75. The $\kappa$ value is typically a value 2 to 3 times the rms error of the system. This is because the above-discussed method for correcting for the effects of eddy current-induced magnetic fields can normally be corrected if the error they cause is within 2 to 3 times the rms measurement error of the system. When the system 20 of this invention is employed as a surgical navigation system, these are the type of errors that would occur by the introduction of routine surgical tools into the space where the object is being tracked. If monitor value $\sigma$ is in this range, step 76 is executed.

However, there may be instances when a large object around which eddy currents form is introduced into the tracking space. In a surgical environment, this could happen, for example, if an aluminum tray is introduced into the space. In this circumstance, given the magnitude of the eddy current-induced magnetic field, the above process steps may not be able to correct for the changes in measured field strength. In this circumstance, $\sigma$ will be above $\kappa$. Once this state is detected, sensor processor 52, in step 77, actuates an alarm 56, also part of system 20. This provides notice to surgical personnel that an object causing unacceptably high eddy currents is in the tracking space and needs to be removed.

In some versions of this embodiment of the invention, the process steps executed to determine the monitor value are executed before the steps used to determine the error values $\delta_{ij}$. This provides individuals using the system fast notification that a significant eddy current-generating object is within the navigation space.

IV. Second Alternative AC-Generated Magnetic Field Sensing System and Method for Eddy Current Correction In a second alternative AC-generated magnetic field sensing system and method of this invention, the same basic transmitter assembly 22 and sensor assembly 24 described with regard to the first alternative system is employed. Here the error values are used to produce a virtual transmitter location and orientation data that is adjusted for the effects of any eddy current-induced magnetic field.

In this method, Equation 13 above is used to calculate the error correction values for one particular transmitter i. The error correction values are then placed into vector form as:

$$\vec{\delta}_i = \begin{bmatrix} \delta_{i1} \\ \delta_{i2} \\ \delta_{i3} \end{bmatrix} \quad (17)$$

Then, the, last calculated rotational matrix R is used to transform vector $\vec{\delta}_i$ from the sensor coordinate system to the fixed transmitter coordinate system by the formula:

$$\vec{\delta}'_i = R \cdot \vec{\delta}_i \quad (18)$$

Figure 7A:
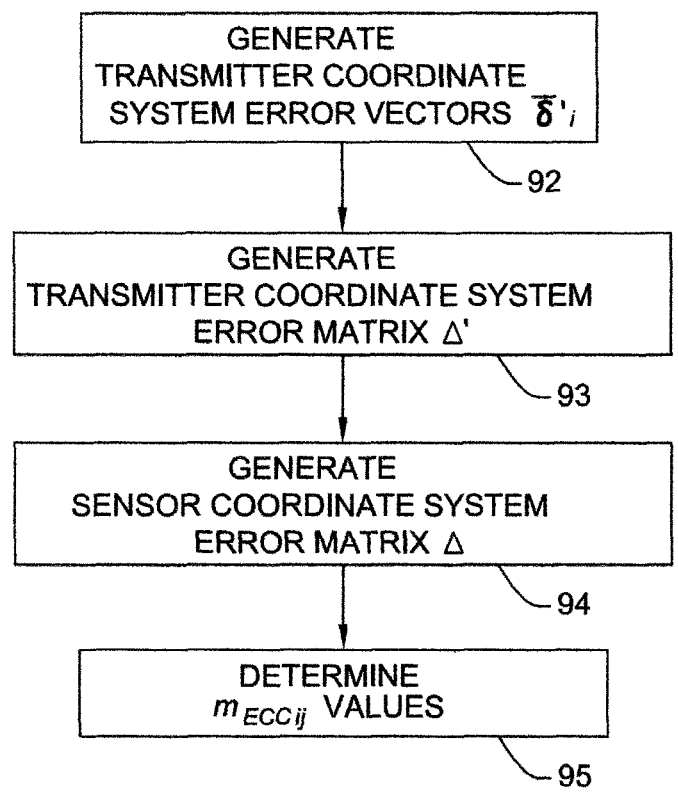
FIG. 7A is a flow chart of an alternative method of determining the error matrix employed in the process of FIG. 7.

In FIG. 7A, the generation of these transmitter coordinate system error vectors is represented by step 92.

Vector $\vec{\delta}'_i$ is then used to form a row in the error correction matrix, step 93. The formation of a matrix using the three vectors $\vec{\delta}'_i$, i=1, 2 and 3, thus forms a transmitter coordinate system error matrix, Δ'.

Then, in a step 94, the transmitter coordinate error matrix Δ' is converted into a sensor coordinate error matrix Δ according to the following formula:

$$\Delta=[R^T \cdot (\Delta')^T]^T \quad (19)$$

Here, $R^T$ is the transpose of the rotational matrix R and $(\Delta')^T$ is the transpose of matrix Δ'.

Once the error matrix Δ is calculated, in a step 95 it is employed in Equation 15 above to determine the $m_{ECCij}$ values from which the position and orientation of the sensor assembly 24 are next determined.

In one preferred version of this embodiment of the invention, the surveillance magnetic fields are based on 20 and 40 Hz signals. The navigation magnetic fields are based on AC signals at 80, 160 and 240 Hz. The surveillance drive signals are applied as a pair of signals to each transmitter 26, 28 and 30 in sequence, for periods of approximately ⅓ second.

In this embodiment of the invention, the above process steps transpose the error matrix so that it is based on the fixed transformer assembly 22. The process is based on the assumptions that (1) from second-to-second the maximum movement of the origin of the sensor coordinate system (tracker) 25 is typically only several centimeters and (2) the change in eddy current-induced magnetic field strength in the navigation space typically does not changer over the distance of this second-by-second movement of the sensor assembly 24.

However, the measured surveillance magnetic field strength for any field emitted from transmitter i as measured by sensor j, $n_{ij}^x$ is based on the following dot product relationship:

$$n_{ij}^x = \vec{B}_i^x \bullet \hat{e}_j \quad (20)$$

Here, $\vec{B}_i^x$ is the surveillance magnetic field x emitted from transmitter i; $\hat{e}_j$ is unit vector of the sensor j at which the measurement of field strength is made. Thus, rotation of tracker, which causes a significant shift in $\hat{e}_j$, results in a like significant change in $n_{ij}^x$. In a surgical procedure, as well as other fields of human endeavor, it is quite simple to rotate the sensor assembly 24 between 20 and 30° within a second. Such rotation significantly changes the error values $\delta_{ij}$ forming error matrix Δ.

To correct for this problem, the above steps are executed to first transform the errors caused by the eddy current-induced magnetic field into the fixed coordinate system of the point (localizer) 31. This transformation produces the fixed coordinate system error matrix Δ'. Then, Equation 19 is employed using the most recently calculated rotational matrix R to determine the error matrix Δ for the sensors. Once the elements of matrix Δ are generated, Equation 15 is executed to determine the eddy current-corrected measurements, the $me_{ECCij}$ values, for the navigation magnetic fields.

This version of the invention makes it possible to perform AC-signal navigation using magnetic fields generated at relatively high frequencies, here, starting at 80 Hz, and still correct for the low strength eddy current-induced magnetic fields.

V. Third Alternative AC-Generated Magnetic Field Sensing System and Method

Figure 9:
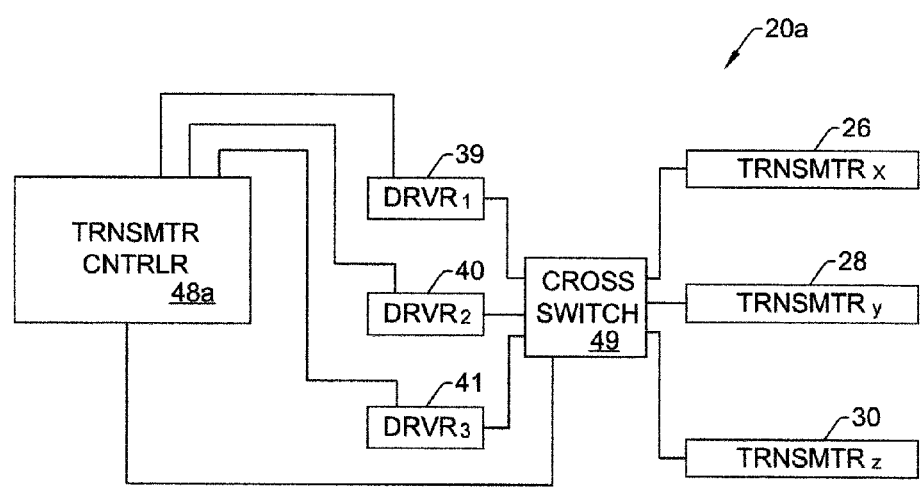
FIG. 9 is a block diagram of an alternative transmitter assembly of AC signal magnetic field navigation system of this invention.

FIG. 9 illustrates an alternative system 20a of this invention. System 20a includes the previously described transmitters 26-30, drivers 39-41 and transmitter controller 48. Drivers 39, 40 and 41 are configured to generate AC signals at, respectively, 20 Hz, 40 Hz and 80 Hz.

System 20a is further configured so that each driver 39, 40 and 41 is selectively connectable to each one of the transmitters 26, 28 and 30. In FIG. 9, this selective connection is shown by the output signals of the drivers 39-41 functioning as input signals to a cross switch 49. The output signals from cross switch 49 are applied to the transmitters 26, 28 and 30. Cross switch 49 is configured to simultaneously apply a separate one of the output signals from each driver 39, 40 and 41 to each of the transmitters 26, 28 and 30. Control signals asserted by transmitter controller 48a to cross switch 49 regulate, at any given instant, to which transmitter 26, 28 or 30, each driver 39, 40 and 41 outputs its driver signals.

The sequence in which the drive signals are applied to each transmitter 26, 28 and 30 is illustrated in the timing diagram of FIG. 10. During three successive periods, n, n+1 and n+2, the following are the frequencies of the navigation magnetic fields emitted by transmitter 26: 20 Hz; 80 Hz; and 40 Hz. Simultaneously, navigation magnetic fields at the following frequencies are emitted from transmitter 28: 40 Hz; 20 Hz; and 80 Hz. During the n, n+1 and n+2 time periods, the navigation magnetic fields are emitted by transmitter 30 at the following frequencies: 80 Hz; 40 Hz; and 20 Hz. After period n+2, the sequence repeats.

Figure 11:
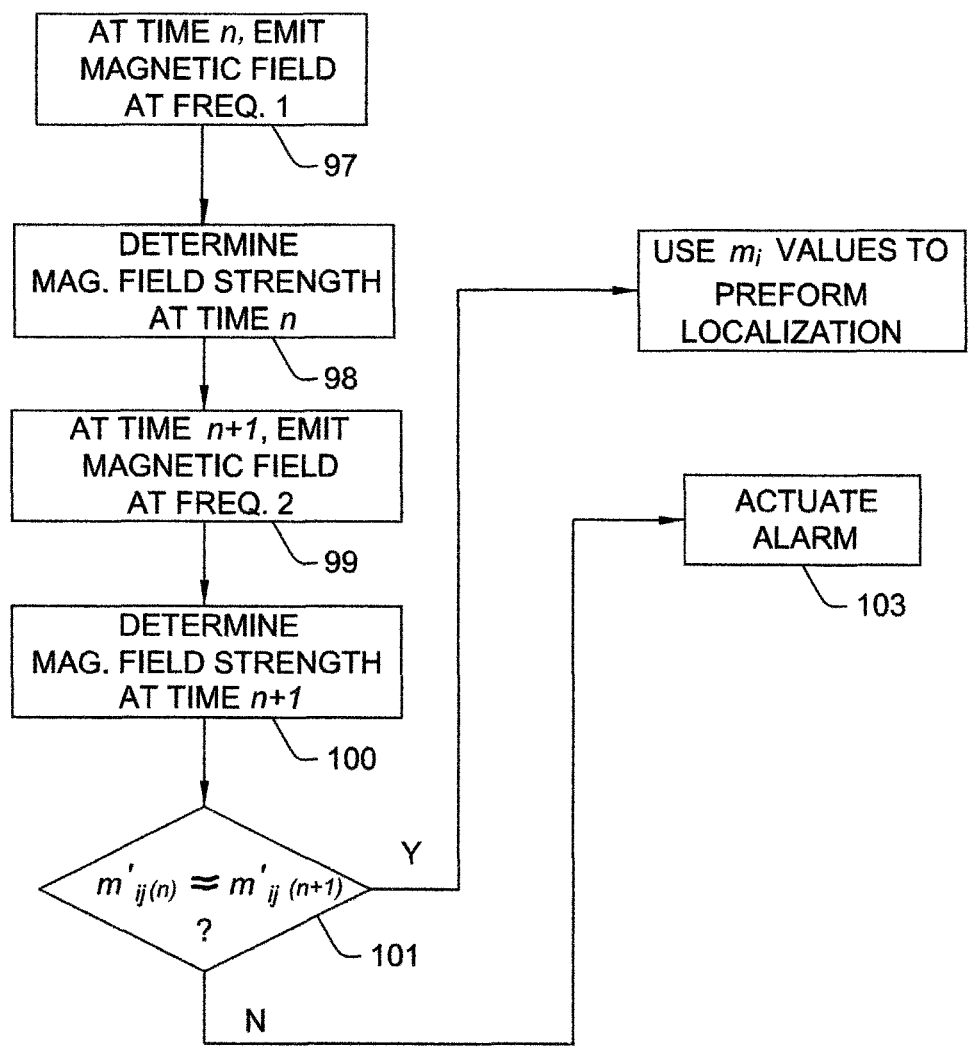
FIG. 11 is a flow chart of the process steps executed during the operation of the system of this invention described with respect to FIG. 9.

Steps 97 and 99 of FIG. 11, represent the emission of magnetic fields at times n and n+1, respectively, from transmitter 26. Also, in steps 97 and 99, the navigation magnetic fields are simultaneously emitted from transmitters 28 and 30.

During any given time period, the strengths of the three navigation magnetic fields emitted by transmitters 26, 28 and 30 are simultaneously measured by sensors 32, 34 and 36. In FIG. 11, these steps for time periods n and n+1 are represented by, respectively, steps 98 and 100. Again, the FFT is used to generate data representative of the strengths of the individual magnetic fields, (step not shown). Based on these data, sensor processor 52 generates the data representative of the position and orientation of the sensor coordinate system (tracker) 25 relative to the transmitter coordinate system (localizer) 23, step 102.

Figure 12:
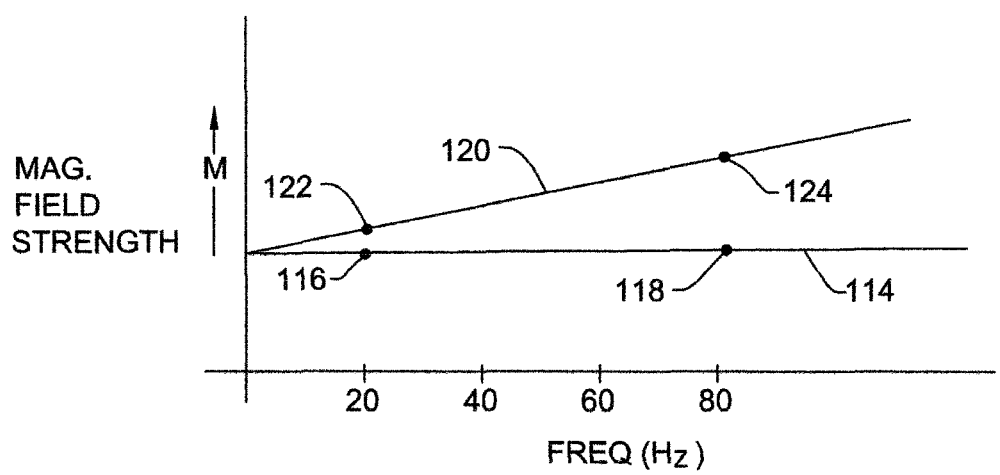
FIG. 12 is a graphical representation how, the strengths of magnetic fields emitted by a common transmitter of the embodiment of the invention illustrated in FIG. 9, over successive time periods, vary as a function of the absence/presence of eddy current-generating objects.

Prior to step 102, sensor processor 52, based on the data representative of magnetic strength, determines whether or not an excessive eddy current-induced magnetic field is present. Sensor processor 52 makes this determination based on the proportional relationship between eddy currents and magnetic fields as illustrated by FIG. 12. Specifically, as seen by horizontal plot 114, in situations wherein no or very low eddy currents are present, the change in measured strength of the navigation magnetic field emitted from a single transmitter 26, 28 or 30 as measured by a single sensor 32, 34 or 36 only nominally changes with frequency.

Therefore, the difference in strength of the magnetic field emitted by a single transmitter 26, 28 or 30 as measured by a given sensor 32, 34 or 36 does not appreciably change between time n when the transmitter emits a magnetic field at 20 Hz and time n+1 when the field is emitted at 80 Hz. This is represented by points 116 and 118 on plot 114. Here, point 116 represents the measured magnetic field strength when a 20 Hz magnetic field is emitted by transmitter 26 as measured by sensor 32, 34 or 36 at time n. Point 118, represents the strength of the magnetic field emitted by the same transmitter 26 as measured by the same sensor at time n+1, when the transmitter emits the field at 80 Hz. The strengths of the measured magnetic field at successive time periods are essentially equal, $$m'_{ij(n)} \approx m'_{ij(n+1)} \quad (21)$$

It should be understood that determination test is between the magnetic field strength measurements that have been normalized, the $m'_{ij}$ values, for differences in field strength of the different frequency signals emitted by the common transmitter 26, 28 or 30. The $m'_{ij}$ measurements are also normalized for any differences in sensitivity of the sensor 32, 34 or 36 due to the sensor's measuring magnetic fields at different frequencies.

When an object that causes large eddy currents to appear is introduced into or near the navigation space, the strength of the eddy current-induced magnetic fields appreciably increases with frequency of the navigation magnetic fields. In FIG. 12, this is represented by diagonal plot 120. Thus, when measurements of the magnetic fields emitted at 20 Hz and 80 HZ in successive time periods from the same transmitter 26, 28 or 30 are measured with the same sensor 32, 34 or 36, the field strength measured in the later period will not be equal to the field strength measured in the initial period, $$m'_{ij(n)} \neq m'_{ij(n+1)} \quad (22)$$

In FIG. 12, this is seen in the difference in measured navigation magnetic field strength along line 120 at points 122 and 124. Point 122 represents the strength of the magnetic field emitted by transmitter 26, at time n when the field is based on a 20 Hz drive signal, as measured by a particular sensor 32, 34 or 36. Point 124 represents the strength of the magnetic field emitted by the same transmitter 26 as measured by the same sensor at time n+1 when the field is based on an 80 Hz drive signal. Here, owing to the added appreciable eddy current-induced magnetic field, the strengths of the fields emitted from the same transmitter are appreciably different even though nothing other than their frequencies has significantly changed.

When an object that induces significant eddy currents is present, there may be phase differences between the navigation magnetic field and the eddy current-induced magnetic field. Owing to these phase differences there may be times when the strength of the second measured magnetic field is appreciably less than that of the first, low-frequency-emitted magnetic field. Thus, the determination of whether or not such object is present is not based on simply determining if the strength of the second measured magnetic field is greater than the strength of the first measured magnetic field. Instead, as indicated by Equations 21 and 22, the relevant process is to determine whether or not the two successive measured navigation magnetic fields are of approximately equal strength.

Thus, sensor processor 52 determines the normalized strengths of the successive 20 Hz and 80 Hz magnetic fields emitted by a single one of the transmitters 26, 28 or 30 as measured by a single one of the sensors 39, 40 and 41 are substantially different. After these determinations are made, in step 101, sensor processor 52 performs the determination of Equation 21. If the measured field strengths are similar, the determination tests true, sensor processor 52 considers the navigation space to be in a state where no significant eddy current-producing object is present. The navigation process, step 102, is executed. Alternatively, if the determination tests false, sensor processor 52 recognizes the navigation space as being in a state in which significant eddy current-induced magnetic fields are present. Sensor processor 52 then, in step 103, actuates alarm 56 so that surgical personnel can clear the space of the object-of-concern.

An advantage of some versions of the above system is that it is does not require a driver or drivers to provide supplemental surveillance magnetic fields. Moreover, this embodiment of the invention uses the same normalized data representative of magnetic strength that is used to determine object position and orientation that to determine if a significant eddy current-producing object is present. This reduces the data processing needed to make this latter evaluation. This frees sensor processor 52 to perform other data calculations.

Moreover, in the system of this version of the invention, the presence of the significant eddy current-producing object is based on magnetic field strength measurements made by the same sensor in successive time periods. In the event point (tracker) 38 is rapidly moved, there is little likelihood such movement could result in a series of successive field strength measurements that do not accurately indicate the absence/presence of an eddy current-producing object.

In order for the above system to operating the navigation magnetic fields should be emitted at frequencies of 500 Hz or less. Preferably, the navigation magnetic fields should be emitted at frequencies of 300 Hz or less. In the most preferred versions of the invention, the navigation magnetic fields should be emitted at frequencies of 150 Hz or less. For operation, the frequency difference between the two magnetic fields should be an order of magnitude of at least 1.5. For improved operation, the order of magnitude difference in frequency should be at least 2. Above the low frequency range, above 100 Hz, the order of magnitude difference between the two frequencies should be even greater, at least 3 if not 4.

VI. DC Pulse-Generated Magnetic Field Sensing System of the Invention

Figure 13:
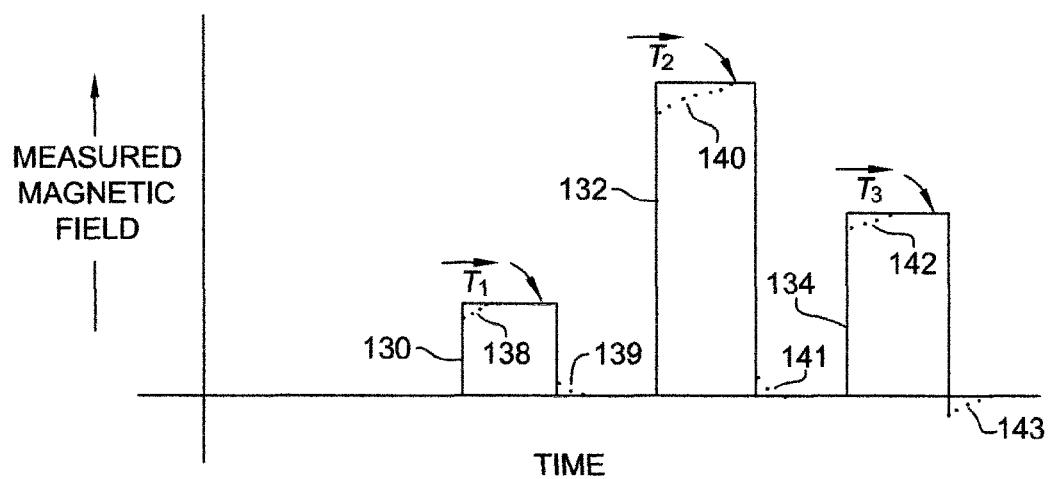
FIG. 13 is a plot of the strengths of magnetic fields measured by a single sensor form three transmitters over time in a DC-signal magnetic field navigation system of this invention.

A DC pulse-generated magnetic field sensing navigation system and method of this invention is now explained by initial reference to the components of FIG. 1 and the plot of FIG. 13. In a DC pulse-generated system, the transmitter controller 48 causes each driver 39, 40 and 41 to emit a short DC-pulse to the associated transmitter 26, 28 and 30, respectively. The pulses are emitted sequentially. The strength of the magnetic field emitted by each transmitter 26, 28 and 30 is simultaneously measured by each sensor 32, 34 and 36. FIG. 13 represents the relative strengths of magnetic field measurements made by a single one of the sensors 32, 34 or 36 of the signals received from each of the transmitters 26, 28 and 30. The magnetic fields measured in the absence of eddy current-generating objects in or adjacent the navigation space is represented by three solid line square wave plots, 130, 132 and 134.

In practice, there is typically a pause of approximately 3 to 15 ms between the emission of one set of DC magnetic pulses and the next set of pulses. For reasons that are apparent below, these pulses are referred to as "navigation" magnetic pulses. The relatively long gap between the emission of each set of navigation magnetic pulses allows the sensor assembly 24 to take measurements of the background (earth) magnetic field.

When the pulses are emitted, drivers 39, 40 and 41 are actuated sequentially so that the navigation magnetic pulses are likewise sequentially individually emitted from the transmitters 26, 28 and 30. Drivers 39-41 are actuated so that a DC magnetic field is emitted individual from each transmitter 26-30 for a period of approximately 1 to 10 ms. There is an approximately 1 to 10 ms quiet period between when the first and second transmitters 26 and 28 emit magnetic fields and between when the second and third transmitters 28 and 30 emit magnetic fields.

If an object around which eddy currents form is present, eddy currents form during DC emission of the pulses as a result of changes in the magnetic field, $\partial \vec{B}_i/\partial t \neq 0$, where $\vec{B}_i$ is the magnetic field emitted as a result of the actuation of transmitter i. Thus, during periods in which the navigation magnetic fields are rising and falling, eddy currents are present.

These eddy currents induce there own magnetic fields that affect the strengths of the navigation magnetic fields measured by the sensors 32-36. In FIG. 13, dotted line pairs 138 and 139, 140 and 141, and 142 and 143 associated with square wave plots 130, 132 and 134, respectively, represent the measurements of magnetic field strength when an eddy current-producing object is present.

The system and method of this invention is based on the principle that the strength of the DC pulse generated field at time t, M(t), is calculated according to the following formula:

$$M(t) = A + \sum_{i=1}^{N} B_i \exp(-C_i t) \quad (23)$$

Constant A is the magnetic field strength of the navigation magnetic pulse. Each $B_i \exp(-C_i t)$ component is an individual one of the components that collectively comprise the eddy current-induced magnetic field.

In practice, it has been found that, only in the initial period after a transmitter 26, 28 or 30 emits a navigation magnetic pulse do the second and higher order $B_i \exp(-C_i t)$ eddy current-induced components appreciably contribute to the magnetic field. The initial period in which these higher order components significantly contribute to the measured magnetic field is typically 1 ms or less. After this period, the contribution of these components goes to zero. After this period, constant A and the first order $B_i \exp(-C_1 t)$ eddy current-induced component collectively provide an accurate estimate of magnetic field strength, over time, of the navigation pulse.

Further, if a magnetic pulse is emitted for an extended period of time, $t \to \infty$, the $B_i \exp(-C_1 t)$ first order eddy-current-induced magnetic field component goes to zero. The magnetic field strength at the sensor 32, 34 or 36, thus becomes based solely on constant A, the magnetic field strength of the navigation magnetic pulse.

Figure 14:
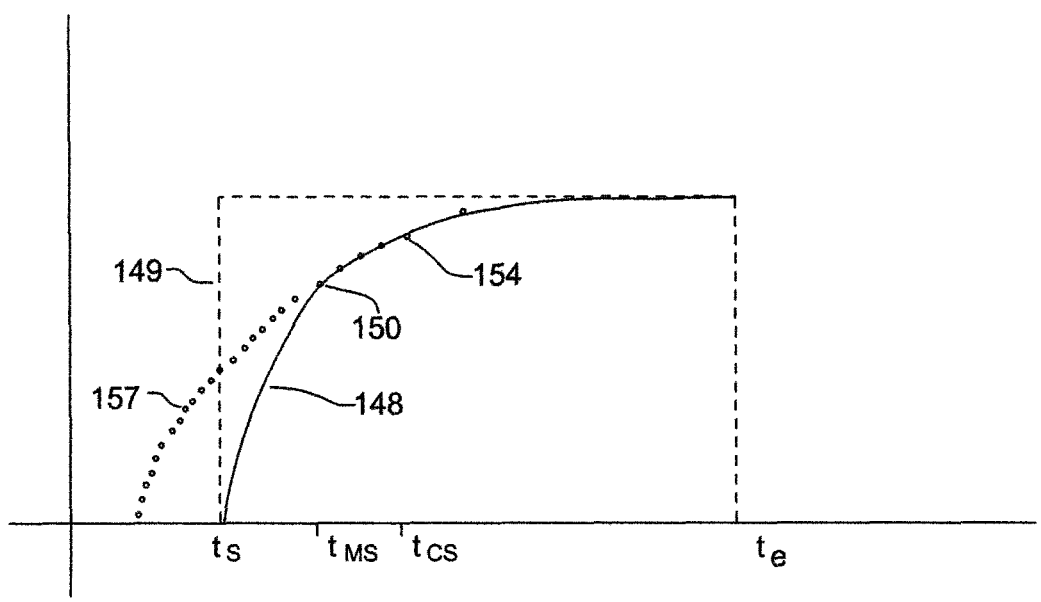
FIG. 14 is a plot of the strength of single DC pulse-generated magnetic field over time and, when, during the period of the pulse, measurements of pulse strength are made according to this invention.

Graphically, these relationships are illustrated in FIG. 14. Solid plot 148 represents the measurement of a magnetic field emitted from a transmitter 26, 28 or 30 as measured over time by a sensor 32, 34 or 36. Dashed line plot 149 represents what would be expected as the measurement of a navigation pulse in an eddy current free environment. (Propagation delays not illustrated.) During an initial period from the start of field emission, time $t_S$ in FIG. 14, to a time at point 150 on plot 148 the field strength measurement increases rapidly with time. This is due to the fact that, initially, the second order and higher eddy current-induced magnetic fields significantly contribute to the composite magnetic field measured by the sensor.

After the time beyond point 150, only the first order eddy current-induced magnetic field and the navigation magnetic field itself contribute to the measured magnetic field. Again, the first order eddy current induced magnetic field decays exponentially over time. Thus, as the time the pulse is emitted increases, the only magnetic field measured is that of the navigation magnetic pulse. This is seen by the merger of plot 148 into plot 149.

Figure 15:
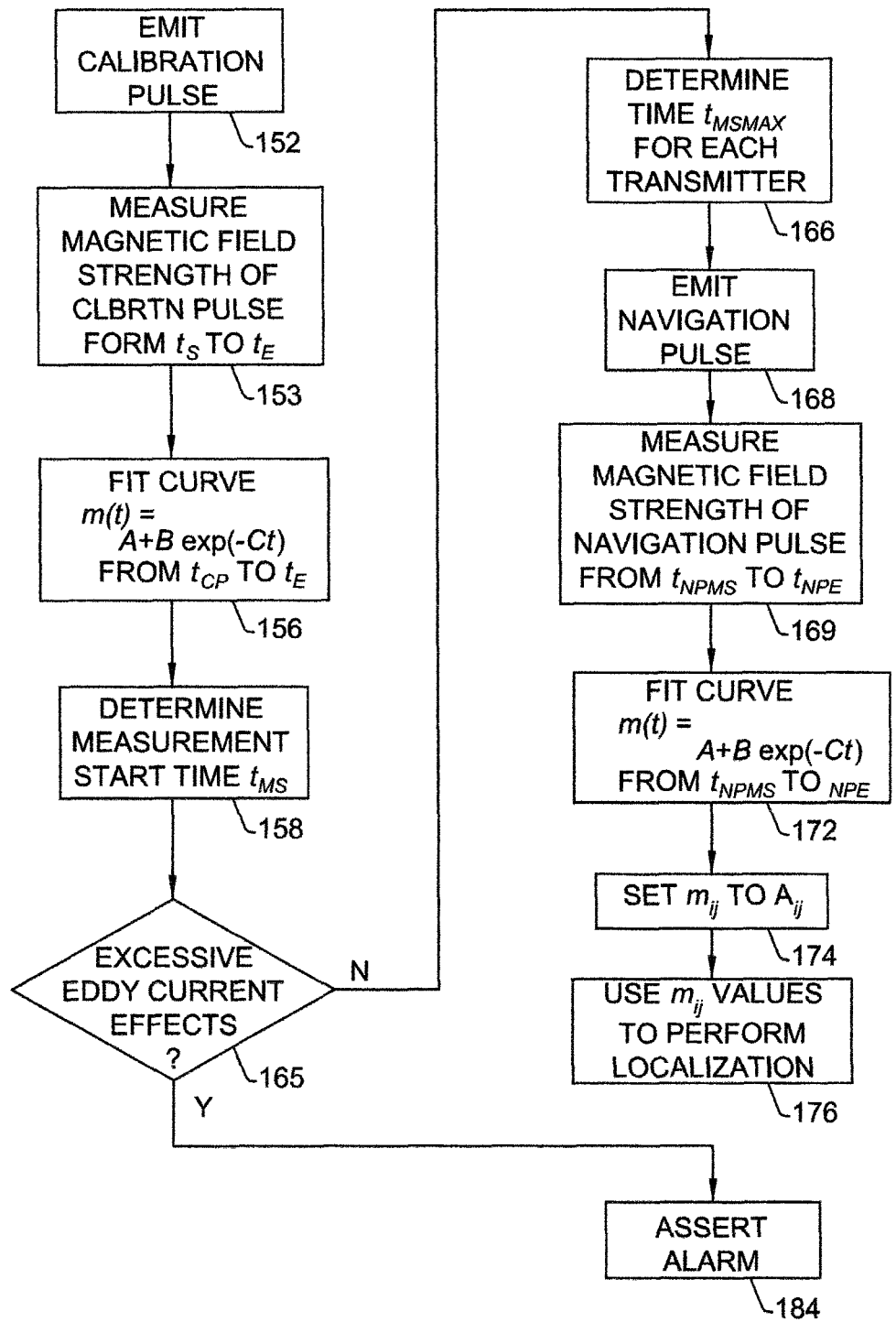
FIG. 15 is a flow chart of the process steps executed by the system of this invention to determine the strength of DC pulse generated navigation magnetic fields when eddy current-induced magnetic fields are also present.

The system and method of this invention takes advantage of the above relationships according to the process steps set forth in FIG. 15. As indicated in this Figure, an initial step 152 of this process is the emission of a DC pulse-generated magnetic field from a transmitter 26, 28 or 30. (Implicit in step 152 is the actuation of the appropriate driver 39, 40 or 41.) This pulse, referred to as a calibration pulse, is between 5 and 12 msec in length. More particularly, this pulse is between 7 and 11 msec in length. Thus, it should be appreciated that calibration pulses are emitted for time periods longer than those in which navigation magnetic pulses are emitted.

Simultaneously with the emission of calibration magnetic field, in step 153, measurements of field strength are made by each sensor 32-36. In a situation wherein and eddy currents are present, the strength of the pulse over time has the profile of solid plot 148 of FIG. 14. Time $t_S$ is the start time of the pulse. Time $t_E$ is the time at which the pulse is no longer emitted. Measurements of strength of the calibration pulse are not needed after time $t_E$.

Then, in step 156, using an exponential curve-fitting function, the measurements of magnetic field strength of the calibration plot from a time $t_{CS}$ to time $t_E$ are used to define a curve according to the following formula:

$$m_{CP}(t) = A_{CP} + B_{CP} \exp(-C_{CP} t) \quad (24)$$

Here, the end result m(t) is the calculated measurement of magnetic field strength at time t; A, B and C are the constant and coefficients of the exponential equation that define m(t). Subscript "$_{CP}$" indicates that these values based on measurements of magnetic field strength for the calibration pulse.

As seen graphically in FIG. 14, the start time, time $t_{CS}$, for the measurements from which $A_{CP}$, $B_{CP}$, and $C_{CP}$ are determined is after the pulse start time $t_S$. Typically, this delay is at least 1 msec. More often, this delay is 1.5 msec or more. On plot 148, point 154 is the start point on the plot from which the curve fitting process is used to determine $A_{CP}$, $B_{CP}$ and $C_{CP}$. Specifically the curve fitting process is used on the data from point 154 to the data collected through time $t_E$.

The constant $A_{CP}$ and coefficients $B_{CP}$ and $C_{CP}$ determined in step 156 do not accurately define the strength of the magnetic field be measured from time $t_S$ to a time before time $t_{CP}$. This is seen in FIG. 14 by a dotted plot 157. Plot 157 represents the calculated values of constant $A_{CP}$ and coefficients $B_{CP}$ and $C_{CP}$ for the period before time $t_{CS}$. Plot 147 it can be seen actually starts, M(t)=0, at a time before time $t_S$. Only starting at the time represented by point 150 does the calculated measurement of magnetic field strength correspond to the actual measurement of magnetic field strength. (From point 150 to point 154 plot 147 overlaps plot 148.)

Thus, in a step 158, sensor processor 52, based on the constant $A_{CP}$ and coefficients $B_{CP}$ and $C_{CP}$, generates an equivalent of plot 157. These data are generated to determine the time when the calculated measurement of magnetic field strength corresponds to the actual measurement of magnetic field strength. In other words, in step 158, the actual measurement of field strength over time and constant $A_{CP}$ and coefficients $B_{CP}$ and $C_{CP}$ are used to determine the time when the measurement at point 150 occurs. This time is referred to as the measurement start time, time $t_{MS}$.

The above process is performed for each transmitter 26-30. (FIG. 15 only illustrates the process for a single transmitter.) A measurement start time $t_{MS}^{ij}$ is thus determined for each transmitter i at each sensor j.

In a step 165, an evaluation is made to determine whether or not excessive eddy current-induced magnetic fields are present. Alternative processes by which this evaluation is performed are discussed below.

For each transmitter 26-30 there is thus a $t_{MS_{MAX}}^{i}$ which is the longest of the three measurement start times $t_{MS}^{ij}$ for the three sensors 32-36. In a step 166, this measurement start time is determined.

The system is then ready to begin tracking of point (tracker) 38. In this process, the system emits from each transmitter a DC pulse generated navigation magnetic field. Step 168 of FIG. 15 represents the emission of single one of these navigation magnetic fields. The system emits the pulse for time period $t_{PP}^i$ for a particular transmitter i according to the following formula:

$$t_{PP}^i = t_{MS_{MAX}}^i + MC \quad (25)$$

Constant MC is the time period over which sensor processor 52 needs magnetic field strength measurements in order to generate the constant and coefficients of the exponential curve of Equation 24. The MC time period is typically 1 or 2 ms. In situations in which the eddy current induced magnetic field is large, and thus the measurement start time $t_{MS_{MAX}}^i$ is larger than 1 ms, the MC time period can be increased to 3 ms or longer.

In a step 169, the strength of the emitted navigation magnetic field over time is measured by each sensor 32-36. More particularly, in step 169, sensor processor 52, records the measurements of magnetic field strength that are obtained from time $t_{MS_{MAX}}^i$ time $t_{NPE}$ for the emitted navigation pulse. Steps 169, and subsequent steps 172, 175 and 176, represent the process steps associated with the measurements made by a single one of the sensors 32, 34 or 36.

Figure 16A:
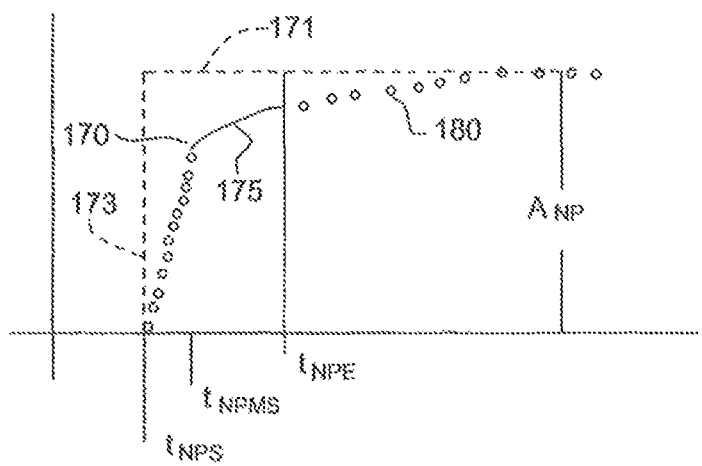
FIG. 16A is a plot of the strength of the measured navigation pulse over time when nominal eddy current-induced magnetic fields are also present.

Plot 170, of FIG. 16a illustrates the field strength of the navigation magnetic pulse emitted in step 168 over time. Time $t_{NPS}$ is the pulse start of the emission. Time $t_{NPMS}$ is the start time for when the magnetic field measurements are taken; the time when step 169 starts. It should be understood that for each transmitter i, time $t_{NPMS}^i$ is the previously determined time $t_{MS_{MAX}}$. Time $t_{NPE}$ is the end time of the emission of the pulse, the time when steps 168 and 169 both terminate. The period between time $t_{NPS}$ and time $t_{NPE}$ is the pulse period time period $t_{PP}^i$ for the transmitter i.

In FIG. 16a, a section 173 of plot 170, from time $t_{NPS}$ to time $t_{NPMS}$, the period in which magnetic field measurements are not taken, is shown as a dotted line. Section 175 of plot 170, shown as a solid line from time $t_{NPMS}$ to time $t_{NPE}$, represents the actual measurements taken of the emitted pulse. Dashed plot 171 represents the strength of the navigation magnetic field if no eddy current-generating objects are present.

In step 172, sensor processor 52, using the measurements of field strength from step 169 determine the constant and coefficients of Equation 24 that define section 175 of plot 170 from time $t_{NPMS}$ to time $t_{NPE}$. Step 172 thus yields the equation:

$$m(t) = A_{NP} + B_{NP} \exp(-C_{NP} t) \quad (26)$$

The subscript "$_{NP}$" denotes navigation magnetic pulse. In this equation, constant $A_{NP}$ is equal to the eddy current effect-free strength of the navigation pulse. In other words, constant $A_{NP}$ is equal to the maximum height, the field strength if the magnetic field represented by plot 171 was measured at sensor j. Thus, in a step 174 each $m_{ij}$ is set to the associated $A_{NP}^{ij}$ constant. These $m_{ij}$ values are employed in the object tracking algorithms employ to determine the position and orientation of point (tracker) 38, step 176.

An advantage of the above arrangement is that it is not necessary to emit navigation magnetic pulses for relatively long time periods. The pulses need only be emitted for a sufficient time to obtain enough data so that curve fitting functions can be used to determine constants $A_{NP}$ and coefficients $B_{NP}$ and $C_{NP}$. This is because these are all the data that are required to determine the apparent strength of the eddy current-effect free navigation magnetic pulse. Graphically this is seen in FIG. 16a. Dotted plot 180 represents the extension of plot 170 after time $t_E$. Plot 180 is obtained by plotting out of Equation 26 as t→∞. Here it seen that, when a constant DC pulse magnetic field is generated, over time, the effects of eddy currents drop to zero. Therefore as seen in this Figure, constant $A_{NP}$ is equivalent to the eddy current effect-free measurement of magnetic field.

In this version of the invention, the measurements from which the eddy current effect-free measurements of navigation pulse magnetic field strength are calculated are measurements from which it is possible to accurately determine constant $A_{NP}$. Since constant $A_{NP}$ is equal to the measure of strength of the navigation magnetic pulse, this means this field strength measurement is accurately calculated.

Moreover, the system and method of this invention, does not rely of field strength measurements taken after all effects of the eddy current-induced magnetic fields have essentially dropped to zero (at a virtual time t=∞). Instead, the system and method of this invention relies on field strength measurements available soon after time $t_{NPS}$. This means that the periods of the navigation pulses can be relatively short, in the nature of 4 msec or less or, sometimes less than 3 msec or even 2 msec or less.

Figure 16B:
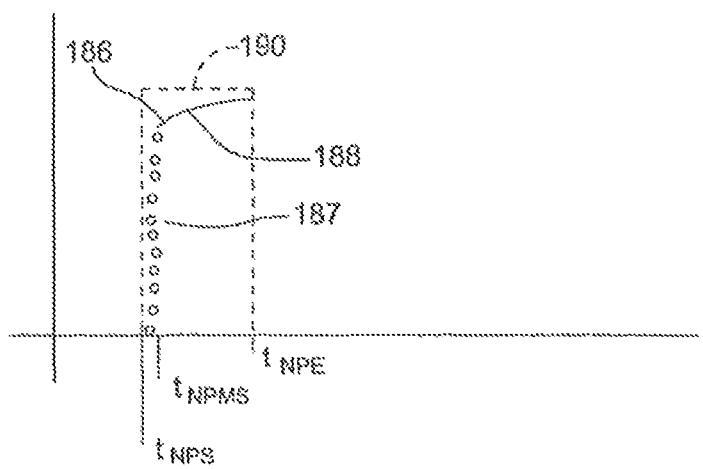
FIG. 16B is a plot of the strength of the measured navigation pulse over time when essentially no eddy current-induced magnetic fields are present.

Another benefit is gained in this embodiment of the invention of the invention by periodically determining updating when magnetic field measurements can be used to determine the strength of the eddy current effect-free navigation pulses, the $t_{NPMS}^i$ navigation pulse measurement start times. This is seen in the comparison of plot 186 of FIG. 16B with plot 170 of FIG. 16A. Plot 186 represents the measure of magnetic field strength over time when there are essentially no eddy currents generating objects present. Initial section 187 of plot 186, shown as a dotted line, in comparison to section 173 of plot 170, has an appreciably stepper slope. Therefore section 188 of plot 186, shown as a solid line, starts at a time sooner to the pulse start time $t_{NPS}$ the start time of section 175 of plot 170. In FIG. 16B, dashed line plot 190 represents the strength of the eddy current-effect free navigation magnetic pulse.

Thus, the measurement start time $t_{NPMS}$ for plot 186, relative to the pulse start time $t_{NPS}$, is sooner than the measurement start time for plot 170. Per Equation 25 above, when this no/low eddy current environment is present, the time periods of the navigation pulses can be shortened. This means the overall frequency of the pulses can be increased to increase the rate at which the object localization position and orientation data are provided.

Alternatively, there may be instances when excessively strong eddy current-induced magnetic fields are present. This situation is represented by measurement of magnetic field strength over time of calibration plot 202 of FIG. 16C. Here dashed plot 204 represents the strength of the measured calibration pulse if eddy current-induced magnetic fields are absent from the navigation space. In this Figure, section 206 of plot 202, shown as a dashed line, represents the field strength measurements when the emission of the electromagnetic pulse causes significant eddy current-induced magnetic fields to be generated. Section 206 of plot 202 has, in comparison to initial section 173 of plot 170, a relatively shallow slope. Section 208 of plot 202, shown as a solid line, represents the measured strength of the calibration pulse after the effects of the second order and higher eddy currents have appreciably subsided.

Figure 16C:
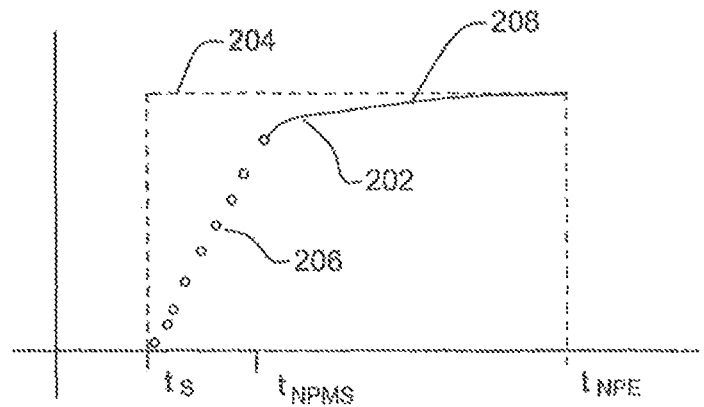
FIG. 16C is the plot of the strength of the measured navigation pulse over time when significant eddy current-induced magnetic fields are present.

From FIG. 16C it can be seen the point in time in which the second order and higher eddy current subside may start before after time $t_{CS}$, the time at which the measurements taken in step 152 start.

In a calibration sequence, the execution of steps 156 and 162 determine if there is a relatively long period of time between start time $t_S$ of the calibration pulse and the calculated measurement time $t_{MS}$. This period may be so long that it is not recommended to perform the object tracking In practice, in step 165 of the calibration process, sensor processor 52 executes one of two algorithms to determine if such a condition exists. In a first process, sensor processor 52, based on the constant and coefficients calculated in step 156, generates a calculated determination to magnetic field strength at the time when the calibration pulse is terminated, time $t_E$. This calculated value is compared to the measured value. If the two values are essentially equal, it is clear that eddy current-induced magnetic fields do not effect the overall measurement of magnetic field strength to such an extent that the field strength of the navigation pulse cannot be accurately determined. The calibration and navigation processes, starting with step 166, can continue.

However, if there is a significant difference in the calculated determination of magnetic field strength at the end of the magnetic pulse, typically the calculated value is less than the measured value, the eddy current-induced magnetic fields are appreciably affecting the ability of the system to generate accurate determinations of navigation pulse magnetic field strength. In such a situation, the only way it may be possible to make such a determination accurately is to appreciably lengthen the time between when the navigation pulse is emitted, and the measured magnetic field strength data are used to generate the pulse strength measurement. Therefore, in step 165, if sensor processor 52 determines there is a significant difference between the measured and calculated determination of magnetic field strength at the end of the pulse, alarm 56 is asserted, step 184.

Alternatively, in step 165, sensor processor 52 compares the deduced measurement start time $t_{MS}$ to a cutoff start time $t_{CUTOFF}$. Time $t_{CUTOFF}$ is a time that, in combination with time constant MC equals the maximum time period, time $t_{PP}$, for which a navigation pulse can be emitted. This time period is based on the minimum frequency at which navigation pulses can be emitted in order for the system to provide sufficiently updated object position and orientation data.

If $t_{MS} \leq t_{CUTOFF}$, then sensor processor 52 determines the effects of any eddy current-induced magnetic fields are not strong enough to affect the localization process. If $t_{MS} > t_{CUTOFF}$, sensor processor 52 interprets the environment as being one in which eddy current-induced magnetic fields of sufficient strength are present to effect the localization process. If this determination is made, sensor processor 52 asserts alarm 56, step 184 is executed.

Thus, the system and method of this version of the invention provide a means to correct for the presence of eddy currents, run at improved efficiency levels when such currents are not present and make a determination when excessive eddy currents that effect localization are present.

VII. First System and Method for Determining the Presence of Ferromagnetic Objects System 20 and method of this invention is also capable of determining if a ferromagnetic object is so close to the navigation space that the object is affecting the ability of the system to accurately perform the localization process.

Figure 17:
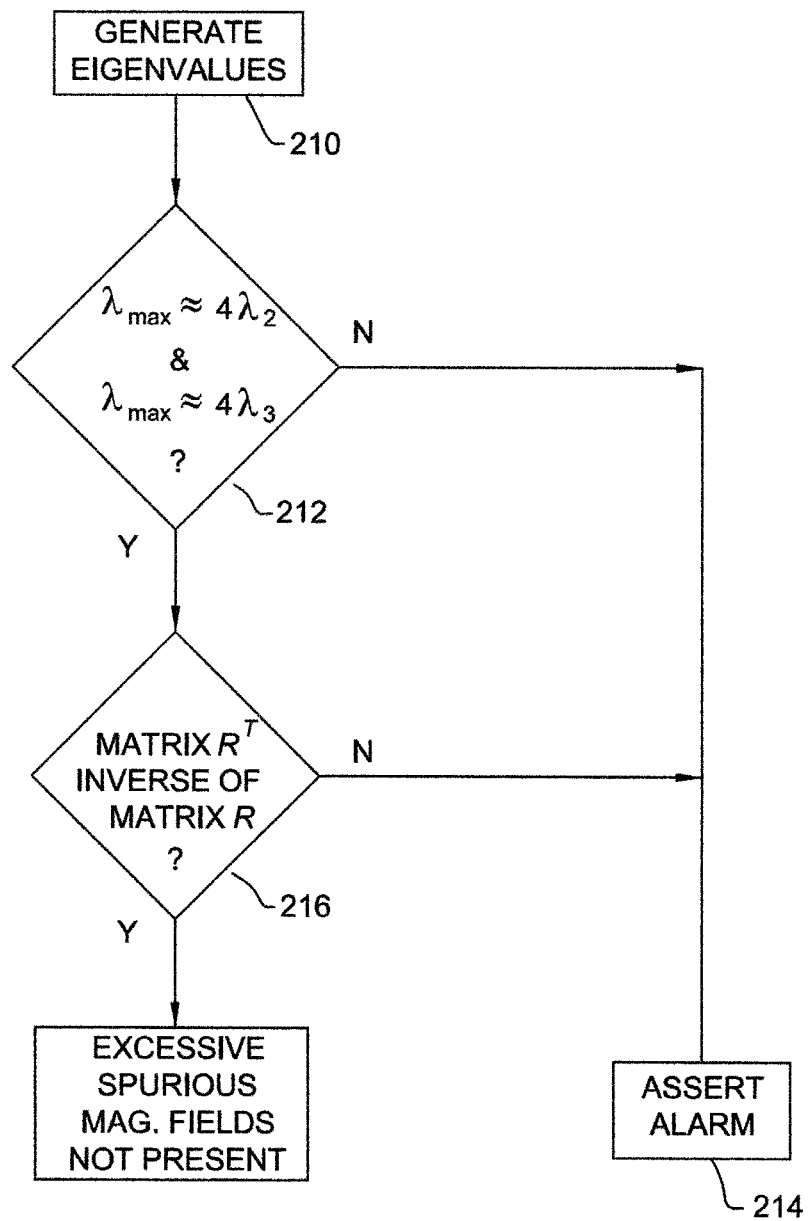
FIG. 17 is a flow chart of the process steps executed according to one method of this invention to determine if spurious electromagnetic fields are present.

In a first embodiment of this process of this invention, as depicted by step 210 of FIG. 17, the eigenvalues of matrix A of Equation 6 above are generated. As discussed above, these eigenvalues and the eigenvector are generated to determine the eigenvalue and eigenvector from which vector $\vec{x}$ is determined. Step 210 produces three eigenvalues $\lambda$.

In, in step 212, the largest of three eigenvalues, $\lambda_{max}$, is compared to the remaining eigenvalues, $\lambda_2$ and $\lambda_3$ multiplied by four (4). If $$\lambda_{max} \approx 4\lambda_2$$

and $$\lambda_{max} \approx 4\lambda_3$$

then sensor processor 52 determines that there are no spurious ferromagnetic object-induced magnetic fields in the navigation space.

The above determination is based on the fact that, if only navigation magnetic fields are present, the magnetic field at the position directly on the dipole axis is twice as large as the magnetic field at positions perpendicular to the dipole. Since the eigenvalues are proportional to the square of their corresponding magnetic fields, this results in the largest eigenvalue having a value that is as four times as the eigenvalues of the remaining two axes. So, if the evaluations of step 212 test true, then significant extraneous magnetic fields are not present.

Alternatively, if appreciable extraneous magnetic fields from ferromagnetic objects or other objects are present, the relationships test for in step 212 will test false. Thus, if the evaluations of step 212 test false, sensor processor 52 recognizes the environment in one in which the appreciable extraneous magnetic fields are present. If this state exists, the sensor processor 52 asserts alarm 56, step 214. The surgical personnel thus have notice that they are to identify and remove the ferromagnetic object in order for the localization process to proceed.

In step 216 a second test of the first version of this feature of the invention is performed to determine whether or not ferromagnetic object-induced magnetic fields are present. In step 216 it is determined whether or not the transpose of the rotational matrix R is also the inverse of the rotational matrix, $$R \cdot R^T = \begin{bmatrix} 1 & 0 & 0 \\ 0 & 1 & 0 \\ 0 & 0 & 1 \end{bmatrix}$$

The above determination tests true if excessive spurious magnetic fields are not present. If the above determination tests false, such fields are present. Therefore, in the event the determination tests false, sensor processor 52 executes step 214 and asserts alarm 56.

The system and method of this embodiment of the invention for determining whether or not ferromagnetic object-induced magnetic fields are present does not require the addition of hardware to the system. Also, the base information from which the determination is made, the eigenvalues and the rotational matrix, are information already generated as part of the object position and orientation determining process. Thus, only a small amount of processing time is required to perform the determination process of this embodiment of the invention.

Figure 18:
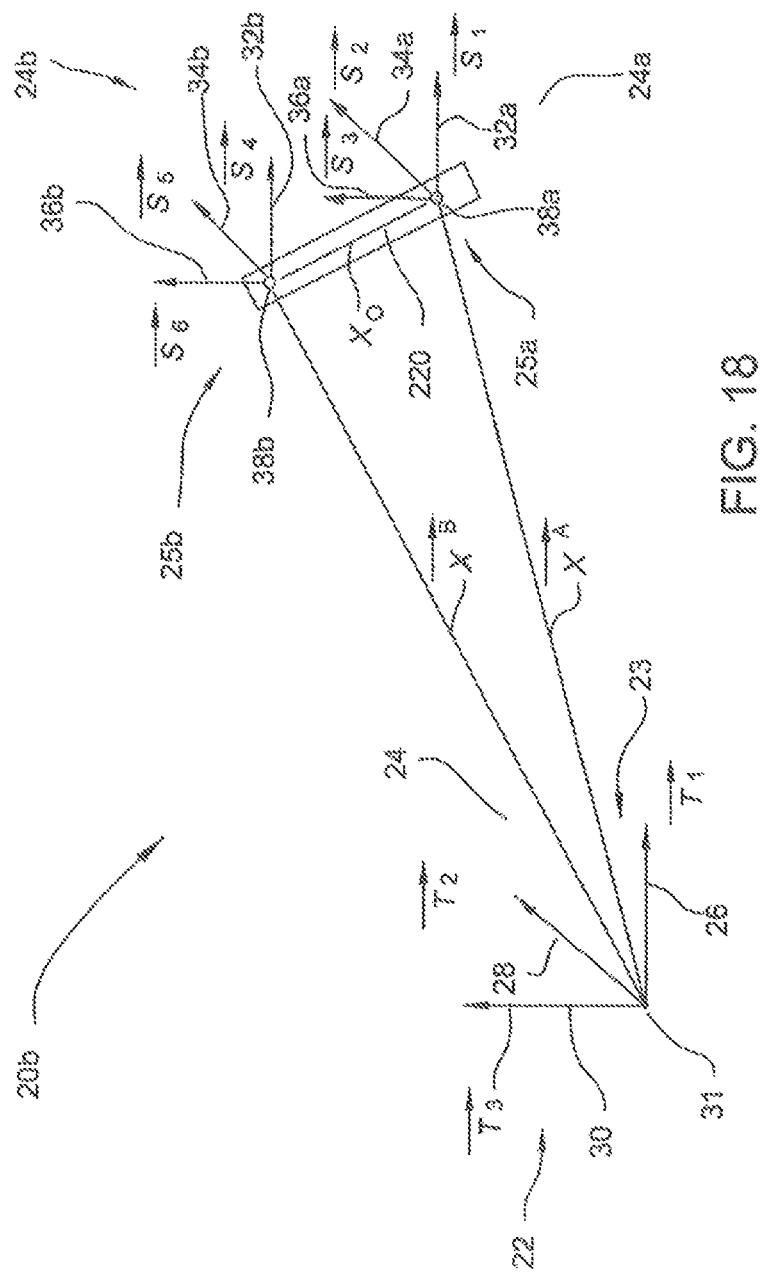
FIG. 18 is a diagrammatic illustrate of a system of this invention that determines if spurious electromagnetic fields are present.
Figure 19:
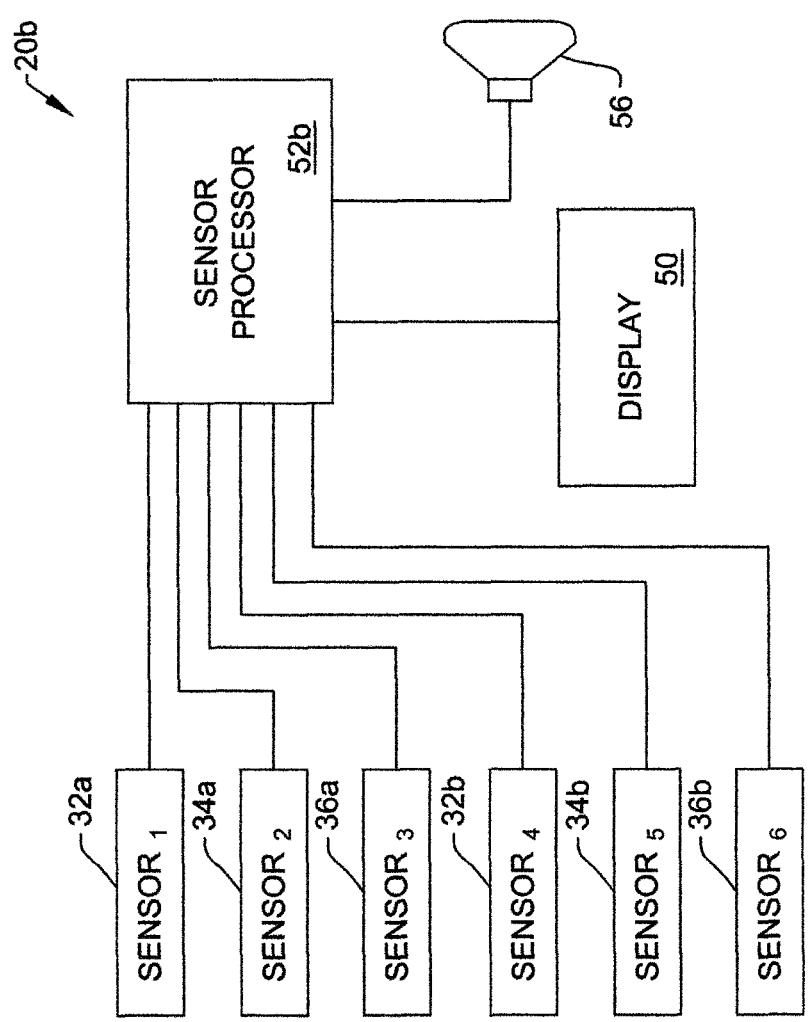
FIG. 19 is a block diagram of the sensor assembly of FIG. 18.

VIII. First Alternative System and Method for Determining the Presence of Ferromagnetic Objects FIGS. 18 and 19 illustrate the structural features of a second embodiment of a system 20b and method of this invention for determining if ferromagnetic objects are present. This version of the invention includes the tracker 220 of FIG. 18. Internal to tracker 220 are two sensor assemblies 24a and 24b. Sensor assembly 24a includes three sensors 32a, 34a and 36a that are arranged orthogonal to each other and centered at point 38a. Mathematically, sensors 32a, 34a and 36a are represented as vectors $\vec{S}1$, $\vec{S}2$ and $\vec{S}3$, respectively. The point 38a and the three sensor vectors $\vec{S}1$, $\vec{S}2$ and $\vec{S}3$ define a first sensor coordinate system 25a. Sensor assembly 24b includes three sensors 32b, 34b and 36b arranged orthogonal to each other and centered at point 38b. Mathematically, sensors 32b, 34b and 36b are represented as vectors $\vec{S}4$, $\vec{S}5$ and $\vec{S}6$, respectively. The point 38b and the three sensor vectors $\vec{S}4$, $\vec{S}5$ and $\vec{S}6$ define a second sensor coordinate system 25b.

Sensor assemblies 24a and 24b are rigidly mounted to tracker 220 so that the geometrical relationship between the two sensor coordinate systems is fixed. Specifically, the distance $x_0$ from point 38a to point 38b is fixed and the rotational matrix $R_0$ that rotates the second sensor coordinate system 25b to align with the first sensor coordinate system 25a is fixed. The distance $x_0$ and matrix $R_0$ are measured in manufacture and stored in the tracker 220 or sensor processor 52a. As seen by FIG. 19, each sensor 32a-36b outputs its sensor signal to the common sensor processor 52a.

This embodiment of the invention includes the basic transmitter assembly 24, drivers 39-41 and transmitter controller 48 of FIGS. 1 and 2.

Figure 20:
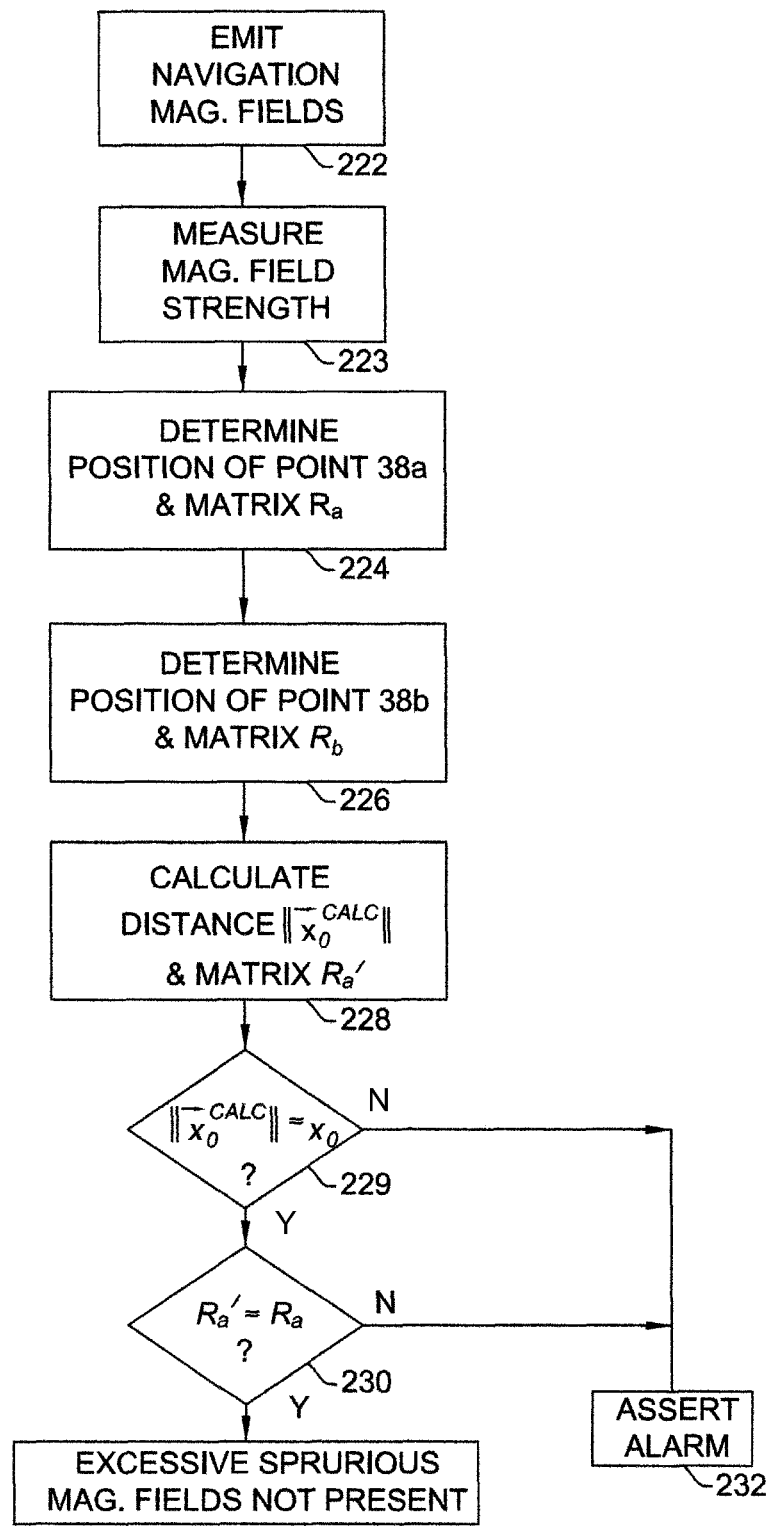
FIG. 20 is a flow chart of the process steps executed by the system of FIG. 18 to determine if spurious electromagnetic fields are present.

The method by which the presence of ferromagnetic objects is determined according to this invention is represented by the flow chart of FIG. 20. In step 222, transmitter assembly 24 emits the navigation magnetic fields. Either AC drive signals or DC pulse signals can be applied in this step to cause the emission of the navigation magnetic fields (pulses). In a step 223, the navigation magnetic fields are received by the sensors 32a-36b; the sensor signals are outputted to sensor processor 52a.

In step 224, based on the measurements of the navigation magnetic fields made by sensor assembly 24a, sensor processor 52a determines the position of point 38a relative to point 31, vector $\vec{x}_a$ of FIG. 18. Here sensor processor 52a also determines the rotational matrix, $R_a$ of the first sensor coordinate system 25a. In step 226, based on the navigation magnetic fields made by sensor assembly 24b, sensor processor 52a determines the position of point 38b relative to point 31, vector $\vec{x}_b$ of FIG. 18. Here sensor processor 52a also determines the rotational matrix, $R_b$, of the second sensor coordinate system 25b.

From position vectors $\vec{x}_a$ and $\vec{x}_b$, in step 228, sensor processor then produces a calculated measurement of the distance between the ends of the vectors, $\|\vec{x}_0^{CALC}\|$. In step 228, sensor processor also calculates a virtual rotational matrix $R'_a = R_0 \cdot R_b$ using the stored $R_0$ that rotates sensor coordinate system 25b to align with sensor coordinate system 25a. In step 229, the distance $\|\vec{x}_0^{CALC}\|$ is compared to the known and stored distance $x_0$ between points 38a and 38b. This comparison is made to determine if:

$$\|\vec{x}_0^{CALC}\| \approx x_0$$

If this determination tests false, alarm 56 is asserted, step 232 is executed.

In step 230, the virtual rotational matrix $R'_a$ is compared to the real rotational matrix, $R_a$, of the first sensor coordinate system:

$$R'_a \approx R_a$$

If the above determination tests true, sensor processor 52a considers the environment to be one in which extraneous electromagnetic waves are not effecting the measurements of the navigation magnetic fields made by sensors 32a-36c. If the determination tests false, step 232 is executed to assert the alarm 56.

The above test are based on the principle that, if the environment is one in which extraneous electromagnetic waves are not effecting the measurements of the navigation magnetic fields made by the sensors, the position and orientation data generated based upon the sensor measurements accurately indicates the position and location of the object being tracked. Therefore, the virtual determination of vector $\vec{x}_0^{CALC}$ and matrix $R'_a$ should be equal to the actual values determined for these variables. It should be understood that data from only one sensor assembly 24a or 24b are needed to provide the object position and orientation data.

Alternatively, if significant extraneous electromagnetic fields are present, including fields generated by ferromagnetic objects, these fields effect the measurements made by the two sensor assemblies 24a and 24b. The effects of these spurious magnetic fields cause inaccurate determinations of the positions of points 38a and 38b. In this situation, the distance $\|\vec{x}_0^{CALC}\|$ between vectors $\vec{x}^A$ and $\vec{x}^B$ will not equal the distance $x_0$ between tracker points 38a and 38b. Similarly, the rotational transformation between rotational matrices $R_a$ and $R_b$ of the two sensor coordinate systems will not equal the rigid geometrical relationship between them. Thus, if either of the above determinations of steps 229 and 230, test false, sensor processor 52a recognizes the environment as being one in which, due to the presence of significant extraneous electromagnetic fields, accurate tracking cannot be performed. In this event, sensor processor performs step 232 to actuate alarm 56.

This method of determining the presence of appreciable spurious electromagnetic fields, including those generated by ferromagnetic objects, provides an almost immediate indication if such fields are present.

Figure 21:
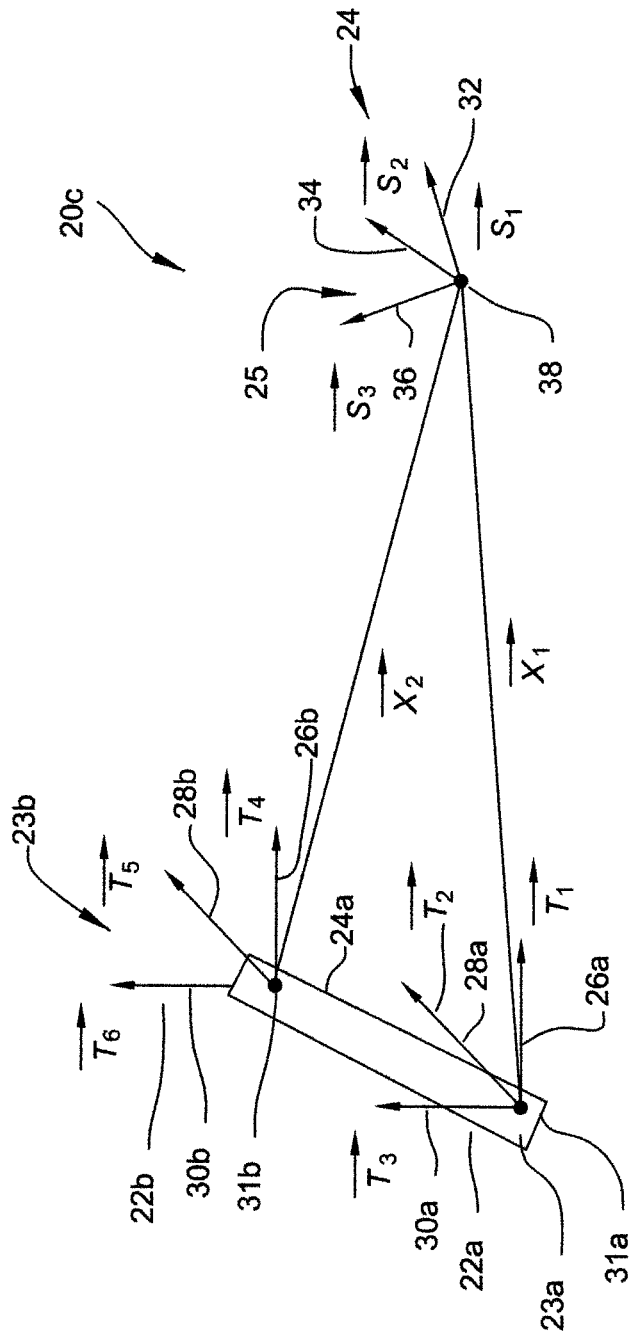
FIG. 21 is a diagrammatic illustrate of a system of this invention that determines if spurious electromagnetic fields are present.
Figure 22:
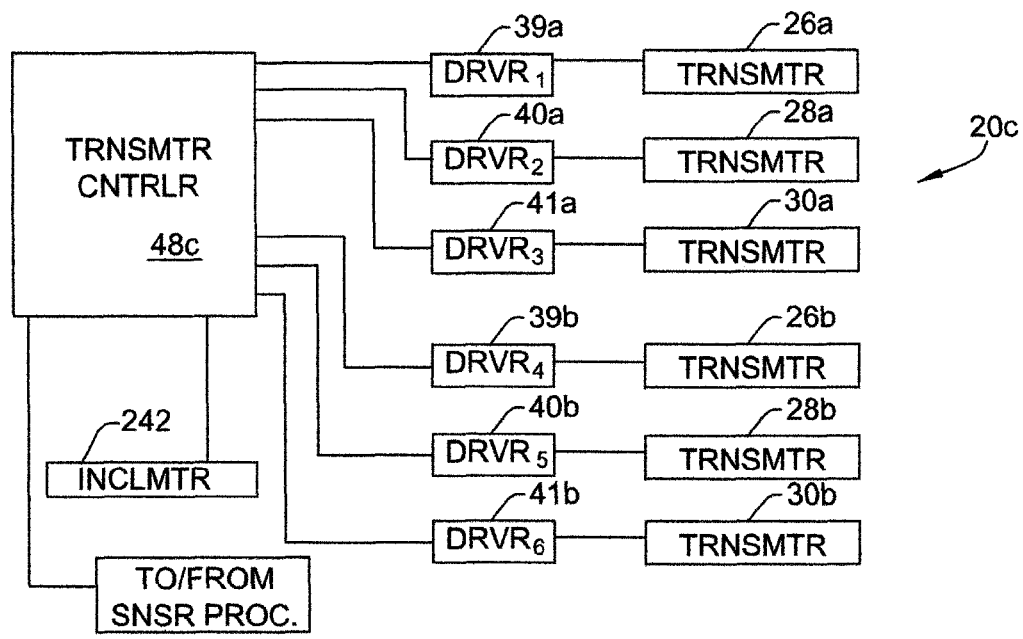
FIG. 22 is a block diagram of the transmitter assembly of FIG. 21.

IX. Second Alternative System and Method for Determining the Presence of Ferromagnetic Objects FIGS. 21 and 22 illustrate a third embodiment of the system and method of this invention that determines whether or not significant ferromagnetic object-induced magnetic fields are adversely affecting the navigation process. System 20c of this version of the invention includes the localizer 240. Localizer 240 has two transmitter assemblies 22a and 22b. Transmitter assembly 22a includes three transmitters 26a, 28a and 30a arranged orthogonally relative to each other and centered around a reference point 31a. Mathematically, transmitters 26a, 28a and 30a are represented as vectors $\vec{T}1$, $\vec{T}2$ and $\vec{T}3$, respectively.

Transmitter assembly 22b includes three transmitters 26b, 28b and 30b arranged orthogonally relative to each other and centered around a reference point 31b. Mathematically, transmitters 26b, 28b and 30b are represented as vectors $\vec{T}4$, $\vec{T}5$ and $\vec{T}6$, respectively. The point 31a and the three transmitter vectors $\vec{T}1$, $\vec{T}2$ and $\vec{T}3$ define a first transmitter coordinate system 23a. Transmitter assembly 22b includes three transmitters 26b, 28b and 30b arranged orthogonally relative to each other and centered around a reference point 31b. Mathematically, transmitters 26b, 28b and 30b are represented as vectors $\vec{T}4$, $\vec{T}5$ and $\vec{T}6$, respectively. The point 31b and the three transmitter vectors $\vec{T}4$, $\vec{T}5$ and $\vec{T}6$ define a second transmitter coordinate system 23b.

The two transmitter assemblies 22a and 22b are rigidly attached to each other. Therefore, the geometrical relationship between the first and second transmitter coordinate systems 23a and 23b, respectively, is fixed. This means mathematically it is possible to derive a coordinate transformation formula that transforms the coordinates in the first transmitter coordinate system 23a to the second transmitter coordinate system 23b. This formula is defined by a translation vector $\vec{x}_0$ and rotational matrix $R_0$. Here $\vec{x}_0$ is the vector from point 31a to point 31b, and $R_0$ is the matrix rotates and aligns vectors $\vec{T}1$, $\vec{T}2$ and $\vec{T}3$ to vectors $\vec{T}4$, $\vec{T}5$ and $\vec{T}6$. Once the translation vector $\vec{x}_0$ and rotational matrix $R_0$ are determined, the coordinates $\vec{x}_b$ of the second transmitter coordinate system for any position can be transformed to the coordinates $\vec{x}'_a$ of the first transmitter coordinate system for the same position by:

$$\vec{x}'_a = R_0 \cdot \vec{x}_b + \vec{x}_0 \quad (27)$$

Any rotation matrix $R_b$ of transmitter coordinate system 23b can also be transformed to the rotation matrix $R'_a$ of transmitter coordinate system 23a by:

$$R'_a = R_0 \cdot R_b \quad (28)$$

Here we use superscript "'" to indicate that $\vec{x}'_a$ and $R'_a$ are transformed values, not the directly measured values from the first transmitter coordinate system 23a. Since the two transmitter assemblies are rigidly attached once the localizer unit is made in manufacture, we can directly measure the translation vector $\vec{x}_0$ and rotational matrix $R_0$ or use a calibration procedure to derive them. It is also possible to use an in-field calibration procedure to update them in case the rigid relationship between the two transmitter assemblies is changed due to shipping or other factors. Nevertheless, one determines the translation vector $\vec{x}_0$ and rotational matrix $R_0$ prior to surgical navigation and stored them in the localizer for use during surgery.

In the illustrated AC drive signal version of the invention of FIG. 22, drive signals are applied to each transmitter 26a-30b by individual drivers. Specifically, drivers 39a, 40a and 41a, respectively, provide the AC drive signals to transmitters 26a, 28a and 30a. Drivers 39b, 40b and 41b, respectively, provide the AC drive signals to transmitters 26b, 28b and 30b. In this version of the invention, drivers 39a-41b drive signals at separate frequencies. For example, in one version of the invention, Table 1 lists the frequencies of the drive signals emitted by the drivers.

TABLE 1

Frequencies of Drive Signals Emitted By The Drivers of FIG. 22.

| Driver 39a | 20 Hz |
| Driver 40a | 40 |
| Driver 41a | 80 |
| Driver 39b | 100 |
| Driver 40b | 140 |
| Driver 41c | 160 |

Transmitter assemblies 22a and 22b are mounted to localizer 240 so that points 31a and 31b are a known fixed distance $x_0$ from each other.

System 20c of this version of the invention also includes the basic sensor assembly 24 described with respect to FIGS. 1 and 3.

Figure 23:
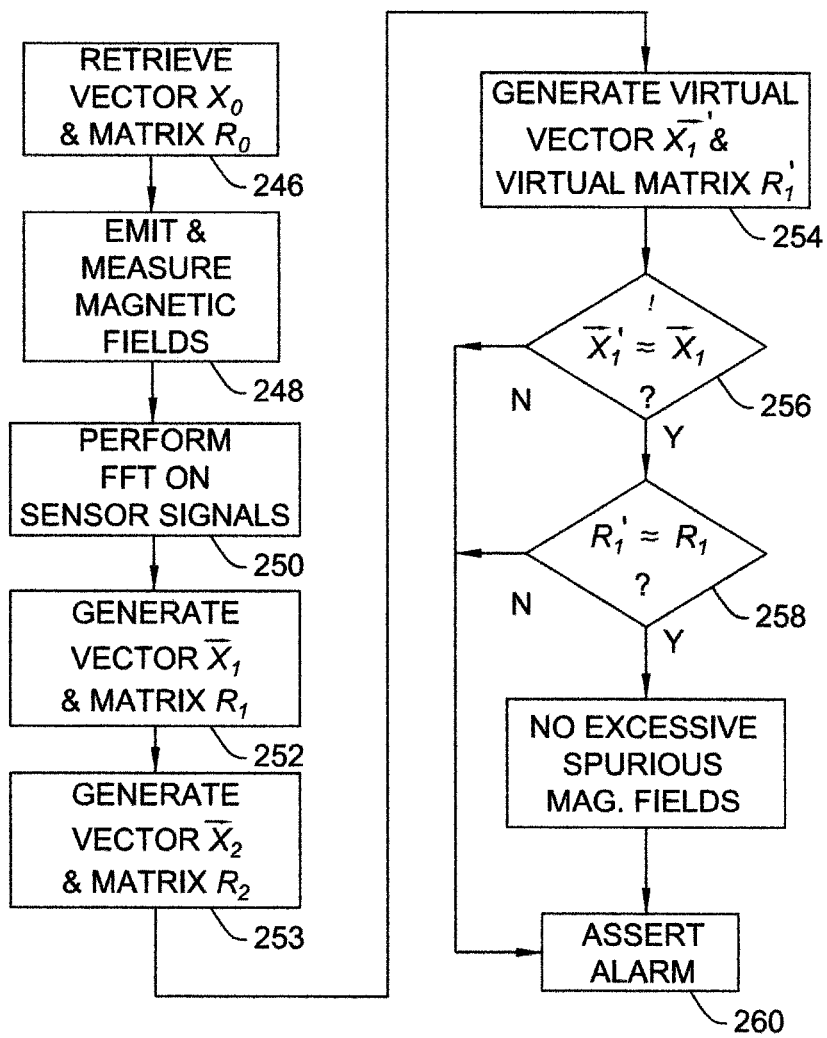
FIG. 23 is a flow chart of the process steps executed by the system of FIG. 21 to determine if spurious electromagnetic fields are present.

The method by which system 20c determines whether or not excessive spurious electromagnetic fields are present in the navigation space is now described by reference to the flow chart of FIG. 23. In a step 246, the localizer also retrieves the stored translation vector $\vec{x}_0$ and rotational matrix $R_0$ which defines the geometrical relationship between transmitter coordinate systems 23a and 23b. If these data are generated by transmitter controller 48c, they are forwarded to sensor processor 52, step not shown.

In a step 248, navigation magnetic fields are simultaneously emitted from each of the transmitters 26a-30b. The fields are simultaneously emitted as a consequence of transmitter controller 48c simultaneously actuating drivers 39a-41b. Also in step 248, sensors 32, 34 and 36 simultaneously measure the strengths of the six emitted navigation magnetic fields.

In step 250, sensor processor 52 performs an FFT on each of the signals generated by sensors 32-36. The FFT for each sensor signal generates six coefficients. The first, second and third order coefficients represent the strengths of the measured fields emitted by the transmitters of transmitter assembly 22a. The fourth, fifth and sixth order coefficients represent the strengths of the measured fields emitted by the transmitters of transmitter assembly 22b.

Based on the nine measurements of field strength of the navigation magnetic fields emitted by transmitter assembly 24a, in step 252, using method described in Section I, sensor processor 52a generates the translation vector $\vec{x}_a$ and rotational matrix $R_a$ of coordinate transformation from sensor coordinate system 25 to transmitter coordinate system 23a. In step 253, based the nine measurements of field strength of the navigation magnetic fields emitted by transmitter assembly 22b, the sensor processor 52a, using the method of Section I, generates the translation vector $\vec{x}_b$ and rotational matrix $R_b$ of coordinate transformation from sensor coordinate system 25 to transmitter coordinate system 23b. Note the translation vectors $\vec{x}_a$ and $\vec{x}_b$ as well as the rotational matrices $R_a$ and $R_b$ are for the same sensor assembly at point 38, but referred to two different transmitter assemblies.

In step 254, using Equation (27), a virtual vector $\vec{x}'_a$ for point 31 in transmitter coordinate system 23a is calculated from the coordinate $\vec{x}_b$ of the same point 31 in transmitter coordinate system 23b. Also in step 254, using Equation (28), a virtual rotational matrix $R'_a$ for sensor axes $\vec{S}_1$, $\vec{S}_2$, and $\vec{S}_3$ in transmitter coordinate system 23a is calculated from the rotational matrix $R_b$ of the same vectors in transmitter coordinate system 23b.

In step 256, the equivalency $\vec{x}'_1 \approx \vec{x}_1$ is tested. In step 258, the equivalency $R'_1 \approx R_1$ is tested. If both equivalencies test true, the sensor processor 52 recognizes the environment as being one in which no spurious magnetic fields are adversely effecting the accurate measurements or determinations of magnetic field strength.

However, if in either step 256 or step 258, the equivalency tests false, sensor processor 52 recognizes the environment as being one in which spurious magnetic fields are adversely affecting the ability of system 20c to accurately track an object. If this determination is made, in step 260, sensor processor actuates alarm 56.

System 20c and the accompanying method of this version of the invention is based on principle that, as long as excessive spurious electromagnetic fields are not present, the virtual determinations of vector $\vec{x}_a$ and rotational matrix $R_a$ based on vectors $\vec{x}_0$ and $\vec{x}_b$ and matrices $R_0$ and $R_b$ should equal the actual determinations of these data because they represent the same position and rotation in a same coordinate system. However, if excessive spurious magnetic fields are present, they unequally effect the navigation magnetic field strength measurements made by sensor assembly 24 of the fields emitted by the two different transmitter assemblies 22a and 22b. If this event occurs, the virtual determinations of vector $\vec{x}_a$ and rotational matrix $R_a$ derived from measurements of transmitter assembly 22b will not equal the equivalent versions of these data based on the measurements made of the transmitter assembly 22a navigation magnetic fields by sensor assembly 24.

System 20c and the companion method of this embodiment of the invention do not require the mounting of additional components in the tracker. Thus, this version of the invention does not require in increase in tracker size in order to provide an indication of whether or not excessive spurious electromagnetic fields are present. Also, given that many navigation systems are provided with plural trackers, the instillation of a single pair of transmitter assemblies, in comparison to installing plural pairs of sensor assemblies, one pair in each tracker, minimizes both system complexity and cost.

It should be appreciated that the process steps executed by system 20c do not have to be emitted each time the system is cycled through a object localization sequence. It is anticipated, the method will be employed only occasionally, for example, once every one to three minutes. Thus, providing system 20c and the accompanying method does not appreciably add to the overall amount of processing time required to perform object localization.

X. Alternative Versions

It should be appreciated that the above describes the basic features of a number of different embodiments of the system and method of this invention. Other versions of the invention are possible.

For example, while in the preferred versions of the invention, each transmitter assembly has three transmitters and each sensor assembly has three sensors, this is not required in all versions of the invention. At a minimum, the system and method of this invention requires at least two transmitters and at least two sensors. In versions of the invention with two transmitters, ideally the sensor assembly should have three sensors. In versions of the invention wherein the sensor assembly only has two sensors, ideally the transmitter assembly should have three transmitters. It should be appreciated the ability of these versions of the system to produce object position and orientation data may be more limited than in the three transmitter and three sensor versions.

Similarly, there is no absolute requirement that the plural transmitters 26-30 be mutually orthogonal or centered around a common point. There is no similar requirement with regard to the sensors 32-36 forming the sensor assembly. However, additional processing steps are then required to generate the object position and orientation data. More specifically, in situations where the transmitters and/or sensors are not co centered or orthogonal, analytical solutions for rotational matrix R and vector $\vec{x}$ such as Equations 5 and 9 will not be possible. However, it is still possible to solve for rotational matrix R and vector $\vec{x}$ by modeling the systems based on physics and solving the non-linear equations by iterative algorithms. Examples of such algorithms are the Levenberg-Marquardt Method, simulated annealing or a genetic algorithm.

Likewise, there is no requirement that in the versions of the invention wherein the AC generated magnetic fields are based on harmonic drive signals, the drive signals and emitted fields be low frequency signals, below 1,500 Hz. As discussed above, this feature of the invention minimizes the effect that any eddy current-generating objects may have on the localization process. However, there may be environments wherein the invention is employed where this matter is not a concern. In these environments, emitting the navigation magnetic fields at higher frequencies can result in a more frequent updating of the object localization data.

Also, in versions of the invention wherein AC generated magnetic fields are emitted that are in a harmonic relationship, there is no requirement that one of the fields be emitted at the base frequency. For example, one could construct a version of this invention wherein AC magnetic navigation fields are emitted at frequencies of 40, 80 and 100 Hz. In this version of the invention, since the emitted signals are harmonics of the 20 Hz base signal, the FFT is used to decompose the composite signal received by each sensor 32, 34 and 36 to determine the strengths of the individual navigation magnetic fields received by the sensor.

In versions of the invention wherein surveillance magnetic fields are emitted simultaneously with the navigation magnetic fields, there is no requirement that any or all of the emitted fields be emitted at a base frequency and its harmonics. As discussed above, emitting fields that have this relationship reduces the processing required to determine the relative strengths of the signals.

Similarly, there is no requirement that, in the methods described with respect to FIGS. 9-11, all signals are emitted at a base frequency and its harmonics. However, for reasons discussed above, it is relatively simple to determine the strengths of the navigation magnetic fields of these versions of the invention.

Further, there is no requirement that plural surveillance magnetic fields always be emitted. In some versions of the invention, it may be possible to emit a single low frequency surveillance magnetic fields while the navigation magnetic fields are emitted at higher frequencies. In this version of the invention the error value $\delta_{ij}$ for the signal emitted by transmitter i and received by sensor j is equal to:

$$\delta_{ij} = m'_{ij} - n''_{ij} \qquad (29)$$

Here, $m'_{ij}$ is the corrected measurement of navigation magnetic field strength; $n''_{ij}$ is the corrected measurement of surveillance magnetic field strength.

In this version of the invention, the corrected measurement of the strength of the surveillance magnetic field, $n''_{ij}$ is also compared to the corrected measurement of navigation field strength, $m'_{ij}$. Specifically, a test is made for the following determination:

$$m'_{ij} \approx n''_{ij}$$

If the determination tests true, then ambient eddy current-induced magnetic fields do not have a significant effect on the measurements of the navigation magnetic fields. If the determination tests false, the ambient eddy current-induced magnetic fields are possibly affecting the ability of the system to accurately determine the strength the true strengths of the navigation magnetic fields.

Thus, it is implicit from the above discussion that the magnetic fields measurements upon which the strength comparisons are made may not just be two navigation magnetic fields or two surveillance magnetic fields. In some versions of the invention, the comparisons of signal strength to determine the magnitude of eddy current-induced magnetic fields may be between a navigation magnetic field and a surveillance magnetic field.

An advantage of these versions of the invention is that they eliminate the need to provide one of the surveillance signal drivers.

Alternatively, when a single surveillance driver is provided, this version of the invention can be combined with one of the other versions of the invention that provides a method for monitoring the strength of extraneous electromagnetic fields. The combined assembly, with a single surveillance driver, both corrects for low strength eddy current-induced magnetic fields and provides an indication of the presence of excessive spurious electromagnetic fields that prevent accurate object localization.

Figure 24:
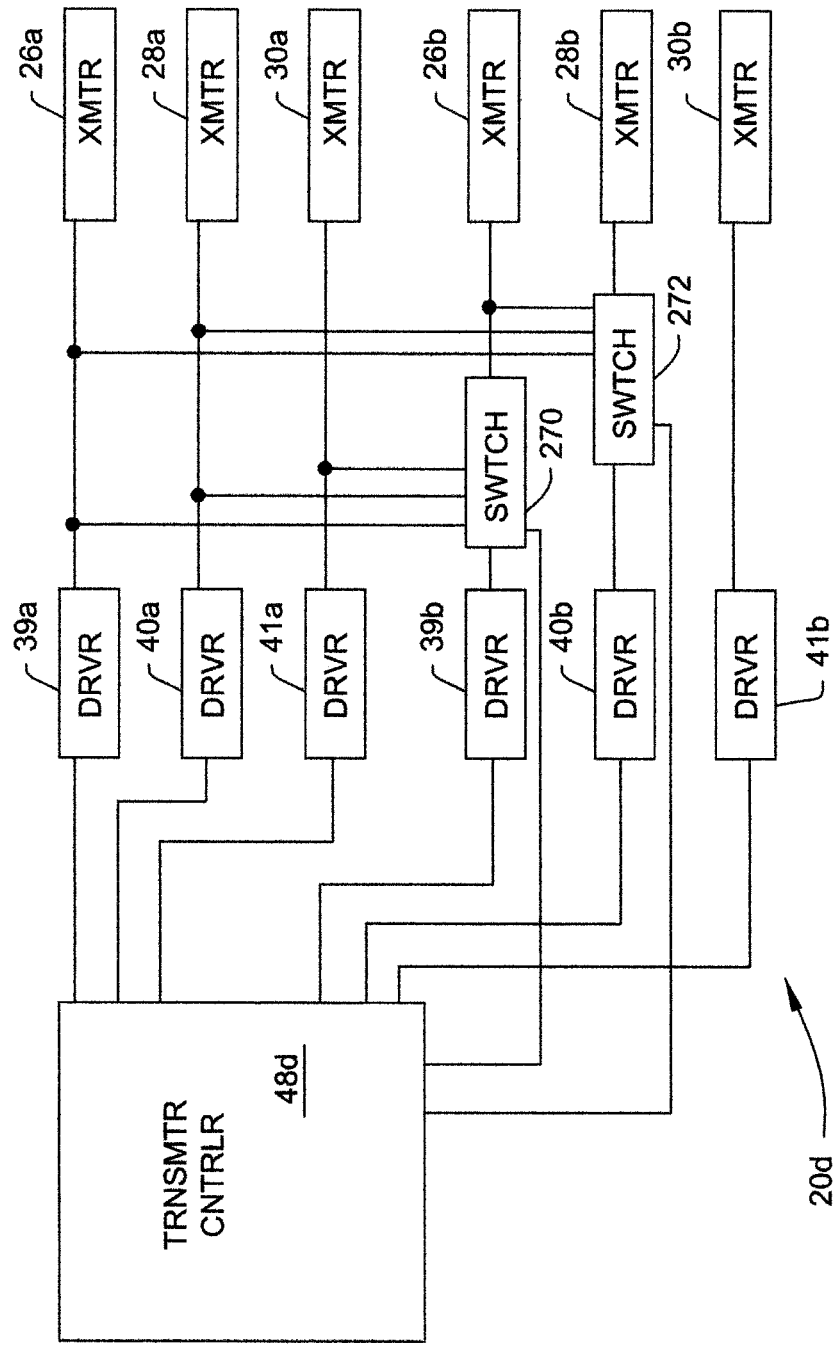
FIG. 24 is a block diagram of an alternative system of this invention.

Another combined version of the invention is illustrated by FIG. 24. Here system 20*d* has the two transmitters 22*a* and 22*b* of system 20*c*. System 20*d* also has the previously described drivers 39*a*-41*b*. A switch 270 connects the output drive signal generated by driver 39*b* to any one of transmitters 26*a*, 28*a*, 30*a* or 26*b*. A switch 272 connect the output drive signal generated by driver 40*b* to any one of the transmitters 26*a*, 28*a* 30*a* or 28*b*. The states of switches 270 and 272 are set by transmitter controller 48*d*. Transmitter controller 48*d* also selectively sets the frequencies of the drive signals emitted by drivers 39*b* and 40*b*.

System 20*d* of this version of the invention operates in two modes. Initially, and then periodically throughout the tracking process, system 20*d* operates in a check mode. In the check mode, transmitter controller 48*d* causes the drivers to output the drive signals identical to those set forth in Table 1. Switch 270 is set so the output signal generated by driver 39*b* is applied to transmitter 26*b*. Switch 270 is set so that output signal generated by driver 40*b* is applied to transmitter 28*b*. The system performs the evaluation described with respect to system 20*c* above to determine whether or not electromagnetic fields that affect the localization process are present.

System 20*d* also operates in a correction mode. In the correction mode, transmitter controller 48*d* causes drivers 39*a*-41*a* to output the same drive signals as in the check mode. Driver 39*b* is set to output a drive signal at 20 Hz. Driver 40*b* is set to output a drive signal at 40 Hz. In this mode, driver 41*b* is deactivated. Switches 270 and 272 are set so the output signals generated by drivers 39*b* and 40*b* are applied simultaneously and in sequence to each of transmitters 26*a*, 28*a* and 30*a*.

Thus, in the correction mode, drivers 39*b* and 40*b* function as surveillance signal drivers. Each transmitter 26*a*, 28*a* and 30*a* periodically emits both navigation magnetic field and the surveillance magnetic fields. Sensor processor 52 then performs the processing steps necessary to produce the eddy current-corrected measurements of navigation magnetic field strength.

System 20*d* both corrects for minor eddy currents and provides an indication when significant extraneous electromagnetic fields are present.

Alternative versions of system 20*a* of this invention are also possible. Thus, there is no requirement that in all versions of the invention the low frequency magnetic field employed as part of the navigation process and to determine the presence of large eddy current-induced magnetic fields always precede the high frequency magnetic field. In some versions of the invention, the sequence in which these fields are emitted may be reversed.

Likewise, it should be appreciated that, in this version of the invention, data describing the difference in signal strength may be filtered over time in order to determine whether or not appreciable eddy current-induced magnetic fields are present. This filtering prevents a single instance of a significant difference in magnetic field strength over two successive time periods from being interpreted as indicating that an eddy current-generating object is nearby. Such differences in measured field strength could also occur if a tracker is rapidly rotated. The filtering of the difference between successive measurements of field strength value thus ensures that, only when the difference is continual over a period of time, for example, approximately 1 second, does the sensor processor 52 interpret the situation as one in which the successive magnetic field measurements indicate the nearby presence of an eddy current-producing object. In such situation, sensor processor 52 then actuates the alarm 56, (step 103 is executed.)

Also, there is no requirement that the determination of this process, the test with regard to Equation 21, be performed on the fields emitted by each transmitter 26-30. In some versions of the invention it may only be necessary to test the successive different frequency fields emitted by a single one of the transmitters. This version of the invention may be simpler to construct or operate than other versions.

Similarly, in another version of the system 20*a* embodiment of the invention, the low frequency drive signal used as part of the eddy current-induced field evaluation may not be one of the navigation drive signals. In these versions of the invention, the signal may come from a surveillance driver. During the operating of this version of system, transmitter controller 48*a*, periodically negates the application of the navigation drive signal to one or more transmitters and momentarily inserts this surveillance drive signal. The relative strengths of the two successive magnetic fields emitted by the same transmitter are compared to determine whether or not the significant eddy current-generating objects are nearby.

FIG. 25 illustrates one sequence in which the surveillance magnetic field is interleaved with the navigation fields. Here, at time periods n, n+2, n+4 and n+6, navigation magnetic fields are simultaneously emitted. The strength measurements of these fields are the data from which sensor processor 52 performs the object localization process. At time n+1, transmitter 26, instead of emitting the 80 Hz navigation magnetic field, emits the Hz surveillance magnetic field. Based on the differences in measured field strength between times n and n+1, sensor processor determines an eddy current correction error correction value and whether or not excessive eddy currents are present. At time n+3, the process is repeated for the 100 Hz navigation magnetic field normally emitted by transmitter 28. At time n+5, the process is repeated for the 140 Hz magnetic field normally emitted by transmitter 30.

This version of the invention thus provides a means to monitor and correct for the presence of eddy current-generating objects while allowing signals above 50 Hz to be used to perform the localization process.

It should likewise be appreciated that the systems and methods of this invention for determining whether or not excessive spurious electromagnetic fields, including the fields generated by ferromagnetic objects, may be incorporated into the versions of this invention that emit either AC or DC pulse magnetic fields.

It should further be understood that in versions of the invention capable of detecting the presence of excessive spurious magnetic fields, the systems may do more than actuate alarm 56. In these embodiments of the invention, the system may also stop generating data representing the position and orientation of the object being tracked. This prevents personnel from taking action based on localization data that may not be accurate.

Moreover, it is further understood that the hardware components of the disclosed versions of the invention are meant to be exemplary, not limiting. For example, in the illustrated version of the system 20*a* embodiment of the invention, the three drivers 39, 40 and 41, each emit a fixed frequency drive signal. These signals are selectively applied to the transmitters 26, 28 and 30 through cross switch 49. In an alternative version of the invention, the drivers 39-41 emit variable frequency drive signals. Each driver 39, 40 and 41 is connected to a separate one of the transmitters 26, 28 and 30, respectively. Control, frequency setting, signals are applied to the drivers 39-41 from the transmitter controller 48*a*. Thus, based on control signals asserted by the transmitter controller 48*a*, each driver 39, 40 and 41 generates a drive signal at an appropriate frequency that causes the associated transmitter 26, 28 or 30 to emit a navigation magnetic field at the appropriate frequency.

Alternatively, the DSP that functions as the transmitter controller 58 during the appropriate time periods adds the surveillance signals to each of the navigation signals. Each composite signal is output to the appropriate driver 39, 40 or 41. An advantage of these versions of the invention is that it eliminates the need to provide multiplexer 58. Similarly, by similarly configuring transmitter controller 48*a* to periodically output different frequency sine waves to the individual drivers 39-41, the need to provide cross switch 49 is eliminated. Transmitter controller 48*d* can likewise be configured in order to eliminate switches 270 and 272.

Similarly some versions of the invention may have plural identical localizers 23 each with its own transmitter assembly 22. These versions of the invention are employed to track an object or multiple objects throughout a space wider that can tracked with a single localizer 23. When constructing these versions of the invention, the spaces covered by the localizers 23 need to overlap so that one can establish the geometric relationship of the individual transmitter coordinate systems.

Also, it may be possible to practice the invention by executing the various process steps in sequences different than what has been described. For example, production of a monitor value σ of step 74 and the comparison of the monitor value to κ of step 75 may occur before the generation of error values and the determination of the corrected magnetic field strength measurements $m_{ECCij}$ of steps 72 and 73

Similarly, methods other than FFT may be used to decompose the composite AC navigation magnetic fields into their individual frequency components. These methods include known analog or digital demodulation techniques.

Therefore, it is an object of the appended claims to cover all such variations and modifications that come within the true spirit and scope of this invention.

What is claimed is:

1. A system for determining the position and orientation of an object, said system comprising:
    a transmitter assembly comprising at least two transmitters, each said transmitter capable of simultaneously emitting plural magnetic fields at different frequencies, wherein said transmitters are configured to:
        simultaneously emit navigation magnetic fields, wherein the navigation magnetic field emitted by each said transmitter is at a frequency different than the frequencies of the navigation magnetic fields emitted by the other said transmitters; and
        with each said transmitter, simultaneously with the navigation magnetic field emitted by said transmitter, emit a plurality of surveillance magnetic fields, the surveillance magnetic fields being at different frequencies and at frequencies less than the frequencies at which said transmitters emit the navigation magnetic fields wherein the surveillance magnetic fields are sequentially emitted by said transmitters so that, after a first said transmitter emits the surveillance magnetic fields, a second said transmitter emits the surveillance magnetic fields;
    at least two sensors, each sensor configured to measure the strength of a composite magnetic field that is the sum of the navigation magnetic fields and the surveillance magnetic fields emitted by said transmitters that are received by the sensor and to generate a sensor signal representative of the strength of the received composite magnetic field; and
    a processor connected to said sensor to receive the sensor signals, said processor is further configured to:
        for each sensor signal, based on the sensor signal from said sensor, determine the strengths of the navigation magnetic fields and the strengths of the surveillance magnetic fields received by said sensor;
        based on the strengths of the surveillance magnetic fields that are transmitted with each navigation magnetic field, determine the strength of eddy current induced magnetic field as a function of field frequency;
        for the navigation magnetic field emitted with the surveillance magnetic fields, based on the strength of the eddy current induced magnetic fields as a function of field frequency and the frequency of the navigation magnetic field, determine an error value for the navigation magnetic field;
        for the navigation magnetic field emitted with the surveillance magnetic fields received by each sensor, based on the strength of the navigation magnetic field and the error value for the navigation magnetic field, generate a corrected measurement of navigation magnetic field strength; and
        based on the corrected measurements of navigation magnetic field strengths for the plurality of navigation magnetic fields that are received by said plurality of sensors, compute position and orientation data for the sensors.

2. The system for determining the position and orientation of an object of claim 1, wherein said processor determines the strength of eddy current induced magnetic fields as a function of frequency for a navigation magnetic field based on the difference in the strengths of the surveillance magnetic fields simultaneously emitted with the navigation magnetic field.

3. The system for determining the position and orientation of an object of claim 1, wherein said processor is further configured to:
    based on the strengths of the surveillance magnetic fields emitted with a navigation magnetic field that are received by a said sensor, determine an average surveillance magnetic field strength; and
    when determining the error value for a navigation magnetic field emitted with the surveillance magnetic fields further determine the error value based on the average surveillance magnetic field strength.

4. The system for determining the position and orientation of an object of claim 1, wherein said transmitter assembly is further configured so that the surveillance magnetic fields emitted by said transmitters are emitted at the same frequencies by each said transmitter.

5. The system for determining the position and orientation of an object of claim 1, wherein said transmitter assembly is further configured so that the surveillance magnetic fields and the navigation magnetic fields are all emitted at harmonics of a common base frequency.

6. The system for determining the position and orientation of an object of claim 1, wherein said transmitter assembly is further configured so that the surveillance magnetic fields and the navigation magnetic fields are all emitted at harmonics of a common base frequency and one of the surveillance magnetic fields is emitted at the first order harmonic of the base frequency.

7. The system for determining the position and orientation of an object of claim 1, wherein said transmitter assembly is further configured so that the surveillance magnetic fields and the navigation magnetic fields are emitted at frequencies of 300 Hz or less.

8. The system for determining the position and orientation of an object of claim 1, wherein said processor is further configured to:
    determine the difference in the strengths of the surveillance magnetic fields simultaneously emitted with each navigation magnetic field;
    based on the difference in the strengths of the surveillance magnetic fields simultaneously emitted with each magnetic field determine if excessive eddy current induced magnetic fields are present;
    if excessive eddy current induced magnetic fields are present, assert an alarm.

9. The system for determining the position and orientation of an object of claim 1, wherein:
    said transmitter assembly is further configured so that each said transmitters, when emitting surveillance magnetic fields simultaneously with the navigation magnetic field, emit the surveillance magnetic fields at power levels less than a power level at which the navigation magnetic field is emitted; and
    said processor is further configured to:
        adjust for differences in the strengths of the surveillance magnetic fields being at lower power levels than the navigation magnetic field with which the surveillance magnetic fields are emitted to generate calibrated measurements of surveillance and navigation magnetic fields strength; and
        use the calibrated measurements of magnetic field strength to determine the corrected measurement of navigation magnetic field strength.

10. The system for determining the position and orientation of an object of claim 1, wherein said processor is further configured to:
    as part of the process of determining the strengths of the navigation magnetic fields and the surveillance magnetic fields that form the composite magnetic field received by sensors, adjust for sensor variations in responsiveness as a function of the frequencies of the magnetic fields received by said sensors so as to produce calibrated measurements of the strengths of the navigation magnetic fields and the surveillance magnetic fields received by said sensors; and
    use the calibrated measurements of the strengths of the measurements in the strengths of the navigation magnetic fields and the surveillance magnetic fields to determine the corrected measurements of navigation magnetic field strength.

11. A method of determining the position and orientation of an object, said method including the steps of:
    simultaneously emitting navigation magnetic fields from a plurality of transmitters wherein, the navigation magnetic field emitted by each transmitter is at different frequency than the navigation magnetic fields emitted by the other transmitters;
    when emitting the navigation magnetic fields from the transmitters, from each transmitter, simultaneously emitting with the navigation magnetic field a plurality of surveillance magnetic fields, wherein, the surveillance magnetic fields are emitted at different frequencies and at frequencies less than the frequencies at which the transmitters emit the navigation magnetic fields wherein, the surveillance magnetic fields are emitted sequentially by the transmitters so that, after a first transmitter emits the surveillance magnetic fields, a second transmitter emits the surveillance magnetic fields;
    simultaneously measuring the strengths of the magnetic fields with a plurality of sensors wherein, each sensor receives the navigation magnetic fields simultaneously emitted by the transmitters and the surveillance magnetic fields sequentially emitted by the transmitters;
    determining the strengths of each navigation magnetic field and surveillance magnetic field received by each sensor;
    based on the strengths of the surveillance magnetic fields measured by a sensor, determining the strength of eddy current induced magnetic fields measured by the sensor as a function of field frequency;
    for the navigation magnetic field emitted by a transmitted when the transmitter emits the surveillance magnetic fields, based on the strength of the eddy current induced magnetic fields as a function of field frequency and the frequency of the navigation magnetic field, determining an error value for the navigation magnetic field measured by the sensor;
    for the navigation magnetic field emitted by a transmitter when the transmitter emits surveillance magnetic fields, based on the determined strength of the navigation magnetic field received by a sensor and the error value, generating a corrected measurement of navigation magnetic field strength; and
    based on the corrected measurements of navigation magnetic field strength for the navigation magnetic fields emitted by the transmitters and received by the sensors, compute position and orientation data for the sensors.

12. The method of determining the position and orientation of an object of claim 11, wherein, in said step determining the strength of eddy current induced magnetic fields as a function of frequency, the strength of the eddy current induced magnetic fields as a function of frequency for a sensor is determined based on the difference in the strengths of the surveillance magnetic fields measured by the sensor.

13. The method of determining the position and orientation of an object of claim 11, further including the step of:
    based on the strengths of the surveillance magnetic fields measured by a sensor, determining an average surveillance magnetic field strength; and
    wherein, in said step of determining the error value for a navigation magnetic field measured by a sensor, determining the error value based on the average surveillance magnetic field strength of the surveillance magnetic fields emitted with the navigation magnetic field.

14. The method of determining position and orientation of an object of claim 11, wherein the surveillance magnetic fields emitted by the transmitters are emitted at the same frequencies by each transmitter.

15. The method of determining position and orientation of an object of claim 11, wherein the surveillance magnetic fields and the navigation magnetic fields emitted by the transmitters are all emitted at harmonics of a common base frequency.

16. The method of determining position and orientation of an object of claim 11, wherein the surveillance magnetic fields and the navigation magnetic fields emitted by the transmitters are all emitted at harmonics of a common base frequency and one of the surveillance magnetic fields is emitted at the first order harmonic of the base frequency.

17. The method of determining position and orientation of an object of claim 11, wherein the surveillance magnetic fields and the navigation magnetic fields emitted by the transmitters are emitted at frequencies of 300 Hz or less.

18. The method of determining position and orientation of an object of claim 11, further including the steps of:
   determining the difference in strengths of the surveillance magnetic fields emitted with a navigation magnetic field that are measured by a sensor;
   based on the difference in strengths of the surveillance magnetic fields measured by a sensor, determining if excessive eddy current induced magnetic fields are present;
   if excessive eddy current induced magnetic fields are present, asserting an alarm.

19. The method of determining position and orientation of an object of claim 11, wherein:
   in said step of emitting surveillance magnetic fields simultaneously with a navigation magnetic field from a transmitter, the transmitter emits the surveillance magnetic fields at power levels less than a power level at which the navigation magnetic field is emitted;
   after said step of measuring the strengths of the magnetic fields with a sensor, calibrating the strengths of the measured fields to adjust for differences in the strengths of the surveillance magnetic fields being at lower power levels than the navigation magnetic field; and
   using the calibrated measurements of magnetic field strength in the subsequent steps to determine the corrected measurement of the strength of the navigation magnetic field emitted with the surveillance magnetic fields and measured by the sensor.

20. The method of determining position and orientation of an object of claim 11, wherein:
   after said step of measuring the strengths of the magnetic fields with a sensor, calibrating the strengths of the measured magnetic fields to adjust for sensor variations in responsiveness as a function of the frequencies of the received signals; and
   using said calibrated measurements of magnetic field strength for the sensor in the subsequent steps to determine the corrected measurement of navigation magnetic field strength.

* * * * *